United States Patent [19]

Kirst

[11] 4,401,660
[45] Aug. 30, 1983

[54] ESTER DERIVATIVES OF 5-O-MYCAMINOSYL TYLONOLIDE AND METHOD OF USING SAME

[75] Inventor: Herbert A. Kirst, Indianapolis, Ind.

[73] Assignee: Eli Lilly and Company, Indianapolis, Ind.

[21] Appl. No.: 330,341

[22] Filed: Dec. 14, 1981

[51] Int. Cl.³ .................. A61K 31/71; C07H 17/08
[52] U.S. Cl. ................................. 424/180; 536/7.1
[58] Field of Search ........... 424/180; 536/17 R, 17 C, 536/7.1

[56] References Cited

U.S. PATENT DOCUMENTS 3,459,853  8/1969  Gorman et al. ................. 424/121
4,092,473  5/1978  Okamoto et al. .................. 536/17
4,299,953  11/1981  Hamill et al. .................... 424/181
4,321,361  3/1982  Baltz et al. ..................... 424/180

FOREIGN PATENT DOCUMENTS 33433  8/1981  European Pat. Off. .

OTHER PUBLICATIONS

A. Tanaka et al. "Synthesis of Recyclized Macrolide Antibiotics and Related Derivatives from Mycaminosyl Tylonolide", *Bull. Soc. Chem. Soc. Japan* 54, 3837–3845 (1981).
A. Tanaka et al. "Synthesis of 4'-Deoxymycaminosyl Tylonolide", *J. Antibiotics* 34, 1374–1376 (1981).
A. Tanaka et al. "Syntheses of Derivatives of 4'-Deoxymycaminosyl Tylonolide and Mycaminosyl Tylonolide Modified at C-23", *J. Antibiotics* 34, 1377–1380 (1981).
S. Omura, Derwent Abstract 82541D/45 of Japanese Kokai J56122-397, Sep. 25, 1981.

Primary Examiner—Johnnie R. Brown
Attorney, Agent, or Firm—Nancy J. Harrison; Arthur R. Whale

[57] ABSTRACT

Ester derivatives of 5-O-mycaminosyl tylonolide (OMT) of the formula

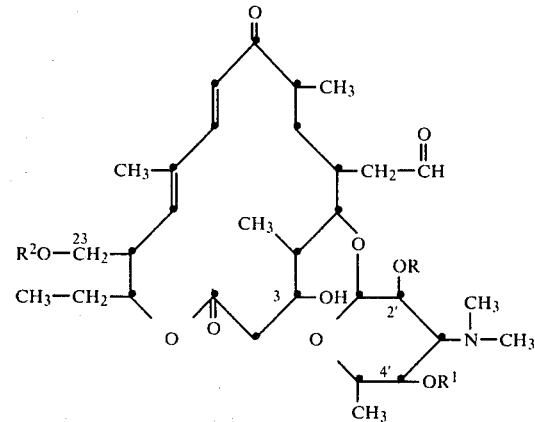

wherein R and $R^1$ are selected from hydrogen, optionally substituted $C_1$–$C_5$-alkanoyl or optionally substituted benzoyl, phenylacetyl, or phenylpropionyl; $R^2$ is hydrogen or an acyl group selected from:

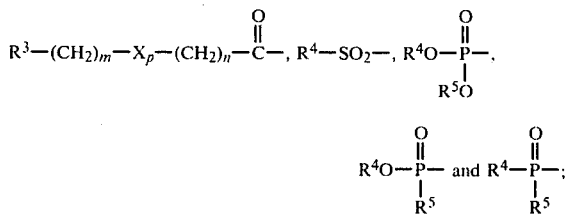

p is 0 or 1; m and n are integers from 0 to 4; $R^3$ is hydrogen, halo, $C_1$–$C_4$-alkyl, $C_3$–$C_8$-cycloalkyl, phenyl, $C_5$–$C_8$-cycloalkenyl, naphthyl, indenyl, tetralinyl, decalinyl, adamantyl, cinnoxacinyl, a monocyclic heterocyclic ring system comprising 3 to 8 atoms in the ring or a bicyclic heterocylic ring system comprising 6 to 11 atoms, provided that at least 1 atom of the ring system is carbon and at least 1 atom of the ring system is a heteroatom selected from O, N, and S; and wherein $R^3$ and the connecting alkyl groups—$(CH_2)_m$— and —$(CH_2)_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —$CH_2$— group; X is O, S, —NH—, —N($CH_3$)—, —C≡C—, —CH=CH—, —C($CH_3$)=CH—, —CH=C($CH_3$)— or —C($CH_3$)=C($CH_3$)—; $R^4$ and $R^5$ are $C_1$–$C_5$-alkyl or optionally substituted phenyl or benzyl; provided that at least one of R, $R^1$ and $R^2$ must be other than hydrogen and that, when $R^1$ is other than hydrogen, R must also be other than hydrogen; and salts thereof; which are useful antibiotics or intermediates to antibiotics, are provided.

119 Claims, No Drawings

ESTER DERIVATIVES OF 5-O-MYCAMINOSYL TYLONOLIDE AND METHOD OF USING SAME

SUMMARY OF THE INVENTION

This invention relates to ester derivatives of 5-O-mycaminosyl tylonolide (OMT) having formula 1:

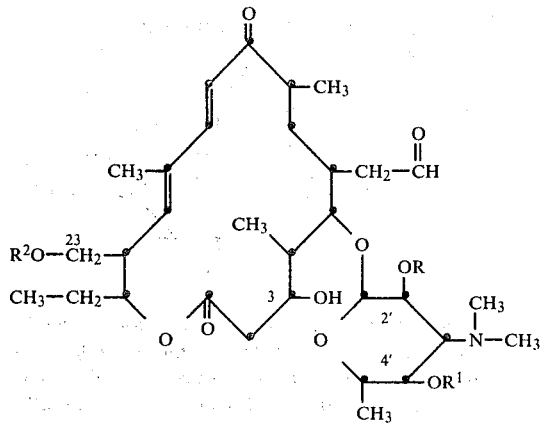

wherein R and $R^1$ are hydrogen, optionally substituted $C_1$-$C_5$-alkanoyl or optionally substituted benzoyl, phenylacetyl, or phenylpropionyl; and $R^2$ is hydrogen or a specified acyl group; provided that at least one of R, $R^1$ and $R^2$ must be other than hydrogen and that, when $R^1$ is other than hydrogen, R must also be other than hydrogen; and to the acid addition salts of these compounds. The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to ester derivatives of OMT and to their acid addition salts. This invention also relates to methods of treating certain infections with, methods of promoting growth in animals with, and pharmaceutical compositions comprising the specified ester derivatives of OMT and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

OMT is an antibiotic described by Marvin Gorman and Robert B. Morin in U.S. Pat. No. 3,459,853, issued Aug. 5, 1969. Ester derivatives of OMT have not previously been described. Esterification of the 23-hydroxyl group of macrolide antibiotics has not been reported because few macrolides have a free hydroxyl group at this position.

Surprisingly, the ester derivatives of OMT of this invention have substantially improved potency over OMT itself.

The ester derivatives of OMT of this invention are compounds of formula 1 wherein R and $R^1$ are selected from hydrogen, optionally substituted $C_1$-$C_5$-alkanoyl or optionally substituted benzoyl, phenylacetyl, or phenylpropionyl; $R^2$ is hydrogen or an acyl group selected from:

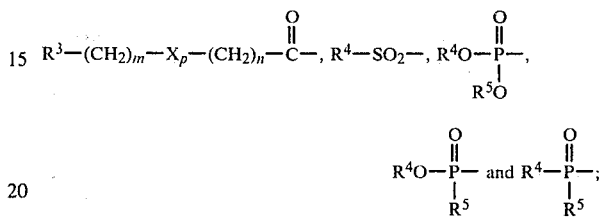

p is 0 or 1; m and n are integers from 0 to 4; $R^3$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl, 1-ethyl-1,4-dihydro-4-oxo[1,3]dioxolo[4,5-g]cinnolin-3-yl(cinnoxacinyl), a monocyclic heterocyclic ring system comprising 3 to 8 atoms in the ring or a bicyclic heterocyclic ring system comprising 6 to 11 atoms, provided that at least 1 atom of the ring system is carbon and at least 1 atom of the ring system is a heteroatom selected from O, N, and S; and wherein $R^3$ and the connecting alkyl groups —$(CH_2)_m$— and —$(CH_2)_n$— are optionally substituted by one or two halo, methyl, ethyl, methoxy, amino, N-protected-amino, methylamino, dimethylamino, nitro, acetoxy, acetamido, azido, carbomethoxy, carboxamido, cyano, or hydroxyl groups, provided that, if the substituent is other than halo or alkyl, there can be no more than one substituent on any connecting —$CH_2$— group; X is O, S, —NH—, —N($CH_3$)—, —C≡C—, —CH=CH—, —C($CH_3$)=CH—, —CH=C($CH_3$)— or —C($CH_3$)=C($CH_3$)—; $R^4$ and $R^5$ are $C_1$-$C_5$-alkyl or optionally substituted phenyl or benzyl; provided that at least one of R, $R^1$ and $R^2$ must be other than hydrogen and that, when $R^1$ is other than hydrogen, R must also be other than hydrogen. The acid addition salts of these compounds are also part of this invention.

The term "optionally substituted $C_1$-$C_5$-alkanoyl" as used herein means an acyl moiety derived from a carboxylic acid containing from one to five carbon atoms. In such a moiety, the alkyl group can be straight, branched, or cyclic and can optionally bear one to three halo substituents. Halo substituents are selected from the group consisting of Cl, Br and F. Acetyl, chloroacetyl, trichloroacetyl, trifluoroacetyl, propionyl, n-butyryl, isobutyryl, n-valeryl, and isovaleryl are examples of such groups.

The terms "optionally substituted benzoyl, phenylacetyl or phenylpropionyl" and "optionally substituted phenyl or benzyl" mean that the phenyl portion of the moiety is optionally substituted by from one to five halo or methyl or by from one to two methoxyl, nitro or hydroxyl groups.

The terms "$C_1$-$C_4$-alkyl" and "$C_1$-$C_5$-alkyl" as used herein mean a straight- or branched-chain alkyl group containing from one to four or from one to five carbon atoms, respectively. Such groups include methyl, ethyl, isopropyl, n-butyl, sec-butyl, isobutyl and tert-butyl and, for the latter, n-pentyl and isovaleryl, and the like.

The term "C$_3$–C$_8$-cycloalkyl" means a saturated ring having from three to eight carbon atoms in the ring. Examples of such rings are cyclopropyl, cyclobutyl, cyclopentyl, cyclohexyl, and cyclooctyl. By "C$_5$–C$_8$-cycloalkenyl" is meant a carbocylic ring which contains from five to eight carbon atoms and which also contains one or two double bonds. Cyclohexadienyl, cyclohexenyl, cyclopentenyl, and cyclooctadienyl are examples of such rings.

The term "monocyclic or bicyclic heterocyclic ring system" as used herein includes saturated or unsaturated heterocyclic moieties containing at least one carbon atom and at least one heteroatom selected from oxygen, nitrogen and sulfur. Heterocyclic groups contemplated include:

unsaturated 3 to 8-membered monocyclic groups, for example, pyrrolyl, Δ$^3$-pyrrolinyl, imidazolyl, pyrazolyl, pyridyl, pyrimidyl, pyrazinyl, pyridazinyl, triazinyl, triazolyl (e.g., 4H-1,2,4-triazolyl, 1H-1,2,3-triazolyl, etc.), tetrazolyl (e.g., 1H-tetrazolyl, 2H-tetrazolyl, etc.), oxazolyl, isoxazolyl, oxadiazolyl (e.g., 1,2,4-oxadiazolyl, 1,3,4-oxadiazolyl, 1,2,5-oxadiazolyl, etc.), thiazolyl, isothiazolyl, thiadiazolyl (e.g., 1,2,4-thiadiazolyl, 1,3,4-thiadiazolyl, 1,2,5-thiadiazolyl, etc.), thienyl, furanyl, etc;

saturated 3 to 8-membered monocyclic groups, for example, pyrrolidinyl, imidazolidinyl, piperidinyl, piperazinyl, morpholinyl, thiazolidinyl, tetrahydrofuranyl, tetrahydrothienyl, tetrahydropyranyl, dioxanyl, etc.;

unsaturated 6 to 11-membered bicyclic groups, for example, indolyl, isoindolyl, coumaronyl, benzothiofuranyl, benzimidazolyl, quinolyl, isoquinolyl, benzopyrazolyl, cinnolinyl, quinazolinyl, benzoxazolyl, benzothiazolyl, benzoxazinyl, coumarinyl, etc.; and the like.

"N-protected-amino" means that the amino group is substituted by a suitable protecting group. Such a group must be one which is compatible with the other functional groups in OMT and which can be readily removed under acidic conditions. One especially suitable amino-protecting group is the tert-butoxycarbonyl (t-BOC) group.

When R$^2$ is acyl and X is —CH=CH—, —C(CH$_3$)=CH—, —CH=C(CH$_3$)—, or —C(CH$_3$)=C(CH$_3$)—, the R$^2$ group can be in either the cis or trans configuration.

Illustrative R$^2$ groups include those wherein:
(1) R$^2$ is

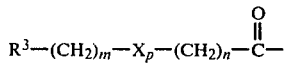

and
(a) R$^3$ is hydrogen or C$_1$–C$_4$-alkyl;
(b) p is 0;
(c) R$^3$ is optionally substituted phenyl;
(d) X is oxygen or —NH— and n is 0; or
(e) X is oxygen or sulfur and n is 1; and
(2) R$^2$ is R$^4$—SO$_2$ and
(a) R$^4$ is C$_1$–C$_5$-alkyl; or
(b) R$^4$ is optionally substituted phenyl.

The compounds of this invention are prepared by esterifying OMT on the 2', 4', and 23-hydroxyl groups by treatment with acylating agents using methods known in the art. The structure of OMT is shown in formula 2:

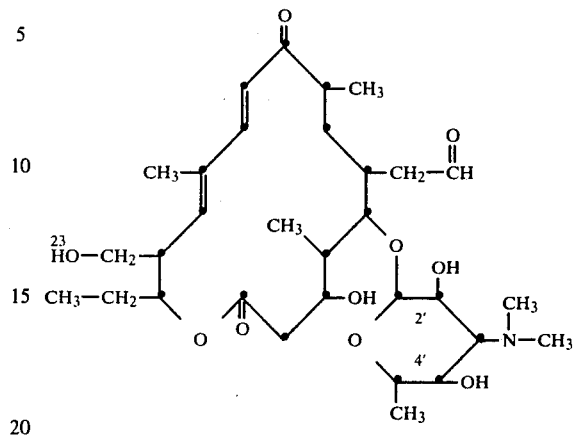

In the absence of external base, esterification of the 2'- and 4'-hydroxyl groups of OMT is more facile than esterification of the 23-hydroxyl group. Typical acylating agents include acyl anhydrides, acyl halides (usually in combination with an acid scavenger), and active esters of organic acids. Acylation can also be achieved by using a mixture of an organic acid and a dehydrating agent such as N,N'-dicyclohexylcarbodiimide. Esterification can be monitored using standard techniques such as thin-layer chromatography (TLC) to determine the time required for the desired reaction. Once formed, the desired ester derivatives can be separated and purified by known techniques.

The 2'-monoester derivatives of OMT can be prepared by acid hydrolysis of mycarose from 2'-ester derivatives of demycinosyltylosin (DMT). DMT and its 2'-ester derivatives are prepared as described by Richrd H. Baltz, Gene M. Wild, and Eugene T. Seno in their co-pending application entitled DEMYCINOSYL-TYLOSIN AND PROCESS FOR ITS PRODUCTION, Ser. No. 156,854, filed June 12, 1980, now U.S. Pat. No. 4,321,361.

A preferred method for the preparation of the symmetrical 2',4'-diester derivatives of OMT, i.e., compounds of formula 1 wherein R and R$^1$ are identical and are other than hydrogen, comprises treating OMT in a neutral solvent such as acetone with a stoichiometric quantity (or a slight excess) of an acylating agent, such as an acyl anhydride, at about room temperature for from about 1 to about 24 hours until esterification of the 2' and 4' hydroxyl groups is substantially complete. The 2',4'-diester derivatives can be isolated from the reaction mixture by standard procedures such as extraction, chromatography and crystallization.

In an analogous manner, the unsymmetrical 2',4'-diester derivatives of OMT, i.e., compounds of formula 1 wherein R and R$^1$ are different, can be prepared by acylation of the appropriate 2'-monoesters of OMT.

The 2',23-diester derivatives of OMT can be prepared by acid hydrolysis of mycarose from the corresponding 2',23-diester derivatives of DMT which are described in my copending application entitled 23-ESTER DERIVATIVES OF DMT, Ser. No. 330,294, filed Dec. 14, 1981.

The 2',4',23-triester derivatives of OMT can be prepared by esterification of the corresponding 2',4'- or 2',23-diester derivatives of OMT. Esterification of the 4'-hydroxyl group of 2',23-diester derivatives of OMT can be accomplished in a manner analogous to the preparation of the 2',4'-diester derivatives. More importantly, 2',4'-diester derivatives of OMT can be converted to 2',4',23-triester derivatives by treatment of the diester with a stoichiometric quantity (or a slight excess) of an acylating agent in the presence of a base, such as pyridine, at from about 0° C. to about room temperature until esterification of the 23-hydroxyl group is substantially complete.

Alternatively, the 2',4',23-triester derivatives of OMT wherein R, $R^1$ and $R^2$ are identical can be prepared by directly esterifying OMT, using the conditions set forth in the preceding paragraph, for a sufficient time to give the triester derivative.

The 23-monoester derivatives of OMT can be prepared from the corresponding 2',23-diester or 2',4',23-triester derivatives of OMT by removing the acyl groups from the 2' or 2',4'-positions. This selective de-esterification can be accomplished using known procedures, such as warming or refluxing in aqueous methanol. The de-esterification reaction can be monitored using standard techniques, such as TLC, to determine the time required for removal of the 2'- or the 2' and 4'-acyl groups.

Alternatively, 23-monoester derivatives of OMT are conveniently prepared by acid hydrolysis of mycarose from the corresponding 23-monoester derivatives of DMT. Preparation of the 23-monoesters of DMT is described in my copending application Ser. No. 330,294.

23-Monoester derivatives of OMT can also be prepared directly from OMT as described in my copending application with John Toth entitled METHOD OF PREPARING 23-MONOESTERS OF OMT AND DMT, Ser. No. 330,295, filed Dec. 14, 1981. This method comprises carrying out the esterification of OMT at low to room temperatures with an appropriately selected acylating agent such as an acyl chloride in the presence of an external base such as 2,4,6-collidine until acylation of the 23-hydroxyl group is substantially complete. The product is isolated using standard procedures.

As has been described, an important method of preparing certain of the ester derivatives of OMT of this invention is by hydrolysis of the corresponding esters of DMT. The structure of DMT is shown in formula 3:

These DMT esters provide useful starting materials for preparation of the corresponding OMT esters because the 4'-hydroxyl group is substituted and thus protected from acylation. The mycarosyl substituent can subsequently be removed by a facile acid hydrolysis once the desired acylations have been performed.

The OMT ester derivatives of this invention form acid addition salts. These acid addition salts are also useful as antibiotics and are a part of this invention. In another aspect, such salts are useful as intermediates, for example, for separating and purifying the OMT ester derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

Pharmaceutically acceptable acid addition salts are an especially preferred group of salts of this invention.

OMT can be prepared by hydrolysis of tylosin, desmycosin, macrocin or lactenocin under mildly acidic conditions as described by Gorman and Morin in U.S. Pat. No. 3,459,853. A preferred method of preparing OMT, by mild acid hydrolysis of DMT, is described by Baltz et al. in Ser. No. 156,854.

DMT is prepared by fermentation of *Streptomyces fradiae* NRRL 12170 under submerged aerobic conditions until a substantial level of antibiotic activity is produced. DMT can be extracted from basified broth filtrate with organic solvents such as ethyl acetate and can be further purified by extraction, chromatography, and/or crystallization. The DMT-producing strain of *Streptomyces fradiae* has been deposited and made part of the stock culture collection of the Northern Regional Research Center, Agricultural Research, North Central Region, 1815 North University Street, Peoria, Ill., 61604, from which it is available to the public under the accession number NRRL 12170.

OMT is prepared from DMT by mild acid hydrolysis. DMT solutions having a pH of about four or below can be used to accomplish the hydrolysis. Temperatures of about 20° to about 100° C. can be used in this method.

3

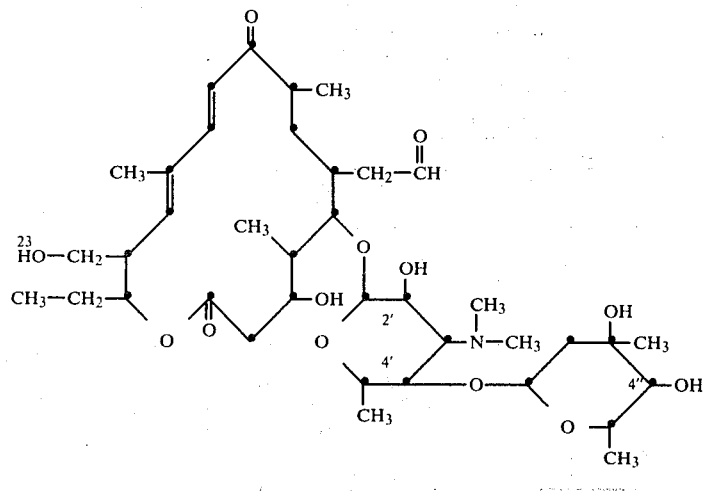

The reaction time needed to carry out the hydrolysis varies, depending upon the pH of the reaction mixture and the temperature used. At higher pH levels the reaction rate is faster. The reaction is carried out by treating DMT with a mild acid solution for a time sufficient to effect removal of the mycarosyl group to give OMT.

Alternatively, and sometimes preferably, OMT can be prepared by treating DMT in the fermentation broth in which it is produced, using mild acidic conditions as above-described for a time sufficient to convert the DMT to OMT. OMT thus prepared can be isolated from the fermentation broth using techniques known in the art.

Illustrative OMT esters of this invention include those compounds of formula 1 listed in Table I.

TABLE I

| Compound No. | R | $R^1$ | $R^2$ |
|---|---|---|---|
| 1 | acetyl | H | H |
| 2 | propionyl | H | H |
| 3 | acetyl | acetyl | H |
| 4 | propionyl | propionyl | H |
| 5 | benzoyl | benzoyl | H |
| 6 | acetyl | acetyl | benzoyl |
| 7 | acetyl | acetyl | acetyl |
| 8 | propionyl | propionyl | propionyl |
| 9 | acetyl | H | acetyl |
| 10 | propionyl | H | propionyl |
| 11 | propionyl | H | acetyl |
| 12 | acetyl | H | propionyl |
| 13 | H | H | acetyl |
| 14 | H | H | propionyl |
| 15 | acetyl | acetyl | n-butyryl |
| 16 | H | H | n-butyryl |
| 17 | acetyl | acetyl | i-butyryl |
| 18 | H | H | i-butyryl |
| 19 | acetyl | acetyl | n-valeryl |
| 20 | H | H | n-valeryl |
| 21 | acetyl | acetyl | i-valeryl |
| 22 | H | H | i-valeryl |
| 23 | acetyl | acetyl | n-octanoyl |
| 24 | H | H | n-octanoyl |
| 25 | acetyl | H | n-octanoyl |
| 26 | H | H | benzoyl |
| 27 | acetyl | acetyl | phenylacetyl |
| 28 | acetyl | H | phenylacetyl |
| 29 | H | H | phenylacetyl |
| 30 | acetyl | H | phenylpropionyl |
| 31 | acetyl | H | (p-chlorophenyl)acetyl |
| 32 | H | H | (p-chlorophenyl)acetyl |
| 33 | acetyl | H | cinnamoyl |
| 34 | acetyl | acetyl | phenoxyacetyl |
| 35 | acetyl | H | phenoxyacetyl |
| 36 | H | H | phenoxyacetyl |
| 37 | acetyl | acetyl | (3,4-dichlorophenylthio)acetyl |
| 38 | H | H | (3,4-dichlorophenylthio)acetyl |
| 39 | acetyl | acetyl | N—(t-butoxycarbonyl)-D(-)phenylglycyl |
| 40 | H | H | N—(t-butoxycarbonyl)-D(-)phenylglycyl |
| 41 | acetyl | acetyl | D(-)mandeloyl |
| 42 | H | H | D(-)mandeloyl |
| 43 | acetyl | acetyl | 3-pyridylacetyl |
| 44 | H | H | 3-pyridylacetyl |
| 45 | acetyl | acetyl | methanesulfonyl |
| 46 | H | H | p-toluenesulfonyl |
| 47 | acetyl | acetyl | (p-acetamidophenyl)sulfonyl |
| 48 | H | H | diphenylphosphoryl |
| 49 | acetyl | i-valeryl | H |
| 50 | acetyl | i-valeryl | i-valeryl |
| 51 | acetyl | i-valeryl | acetyl |
| 52 | phenylacetyl | H | H |
| 53 | phenylacetyl | H | phenylacetyl |
| 54 | H | H | phenylpropionyl |
| 55 | acetyl | acetyl | p-toluenesulfonyl |
| 56 | H | H | (p-acetamidophenyl)sulfonyl |
| 57 | H | H | phenylglycyl |
| 58 | acetyl | H | β-naphthoyl |
| 59 | H | H | β-naphthoyl |
| 60 | acetyl | H | phenyl-n-valeryl |
| 61 | H | H | phenyl-n-valeryl |
| 62 | acetyl | H | (2,5-dimethoxyphenyl)acetyl |
| 63 | H | H | (2,5-dimethoxyphenyl)acetyl |
| 64 | acetyl | H | (p-nitrophenyl)acetyl |
| 65 | H | H | (p-nitrophenyl)acetyl |
| 66 | acetyl | acetyl | dichloroacetyl |
| 67 | acetyl | H | pivaloyl |
| 68 | H | H | pivaloyl |
| 69 | acetyl | H | 1-adamantylcarbonyl |
| 70 | H | H | 1-adamantylcarbonyl |
| 71 | acetyl | H | 4-carbomethoxy-n-butyryl |
| 72 | H | H | 4-carbomethoxy-n-butyryl |
| 73 | acetyl | H | methoxycarbonyl |
| 74 | H | H | methoxycarbonyl |
| 75 | acetyl | H | benzylaminocarbonyl |
| 76 | H | H | benzylaminocarbonyl |
| 77 | acetyl | H | trichloroacetyl |

The OMT ester derivatives of this invention inhibit the growth of pathogenic bacteria, especially gram-positive bacteria, Mycoplasma species and Pasteurella species. For example, Tables II and III show the minimal inhibitory concentrations (MIC's) at which illustrative compounds inhibit certain bacteria. The MIC's in Table II were determined by standard agar-dilution assays. The MIC's in Table III were obtained using a conventional broth-dilution microtiter test.

TABLE II

| | Antibiotic Activity of OMT Ester Derivatives | | | | | | | | | |
|---|---|---|---|---|---|---|---|---|---|---|
| | Test Compound[a] | | | | | | | | | |
| Test Organism | 1 | 2 | 3 | 4 | 5 | 6 | 7 | 8 | 9 | 10 |
| Staphylococcus aureus X1.1 | 2 | 2 | 2 | 2 | 8 | 0.125 | 0.5 | 0.25 | 0.45 | 0.25 |
| Staphylococcus aureus V41[b] | 4 | 4 | 4 | 4 | 32 | 0.25 | 1 | 0.5 | 0.5 | 0.5 |
| Staphylococcus aureus X400[c] | 4 | 4 | 4 | 2 | 64 | 0.25 | 1 | 0.5 | 0.5 | 0.5 |
| Staphylococcus aureus S13E | 4 | 2 | 2 | 2 | 32 | 0.25 | 1 | 0.5 | 0.25 | 0.5 |
| Staphylococcus epidermidis EPI1 | 2 | 1 | 1 | 1 | 8 | 0.25 | 0.5 | 0.25 | 0.25 | 0.25 |
| Staphylococcus epidermidis EPI2 | 2 | 1 | 1 | 4 | 4 | 0.5 | 0.5 | 0.25 | 0.25 | 0.25 |
| Streptococcus pyogenes C203 | 0.5 | 0.5 | 0.5 | 0.5 | 2 | 0.125 | 0.5 | 0.25 | 0.25 | 0.25 |
| Streptococcus pneumoniae Park I | 0.5 | 8 | 0.25 | 8 | 0.5 | 0.06 | 0.125 | 0.25 | 0.125 | 0.125 |
| Streptococcus Group D X66 | 2 | 2 | 2 | 1 | 8 | 0.25 | 1 | 0.5 | 0.5 | 0.5 |
| Streptococcus Group D 9960 | 4 | 2 | 2 | 2 | 8 | 0.25 | 1 | 0.5 | 0.5 | 0.5 |
| Haemophilus influenzae Holt[d] | 4 | 4 | 2 | 4 | 64 | 2 | 2 | 2 | 1 | 2 |
| Haemophilus influenzae R252[e] | 4 | 4 | 4 | 4 | 64 | 2 | 8 | 4 | 4 | 8 |

TABLE II-continued
Antibiotic Activity of OMT Ester Derivatives

| Test Organism | 11 | 12 | 13 | 14 | 15 | 16 | 17 | 18 | 19 | 20 |
|---|---|---|---|---|---|---|---|---|---|---|
| Staphylococcus aureus X1.1 | 0.5 | 0.5 | 0.25 | 0.25 | 0.25 | 0.25 | 1 | 0.25 | 0.25 | 0.25 |
| Staphylococcus aureus V41 | 1 | 0.5 | 0.25 | 0.25 | 0.5 | 0.25 | 1 | 0.5 | 0.25 | 0.25 |
| Staphylococcus aureus X400 | 1 | 0.5 | 0.5 | 0.25 | 0.5 | 0.5 | 1 | 0.5 | 0.5 | 0.5 |
| Staphylococcus aureus S13E | 0.5 | 0.5 | 0.25 | 0.25 | 0.25 | 0.25 | 1 | 0.25 | 0.25 | 0.25 |
| Staphylococcus epidermidis EPI1 | 0.5 | 0.25 | 0.25 | 0.125 | 0.25 | 0.25 | 0.5 | 0.25 | 0.125 | 0.25 |
| Staphylococcus epidermidis EPI2 | 0.5 | 0.25 | 0.25 | 0.125 | 0.5 | 0.25 | 1 | 0.5 | 0.125 | 0.25 |
| Streptococcus pyogenes C203 | 0.5 | 0.25 | 0.125 | 0.125 | 0.25 | 0.25 | 1 | 0.5 | 0.25 | 0.25 |
| Streptococcus pneumoniae Park I | 0.25 | 0.125 | 0.125 | 0.125 | 0.25 | 0.06 | 0.25 | 0.25 | 0.03 | 0.06 |
| Streptococcus Group D X66 | 1 | 0.5 | 0.25 | 0.25 | 0.5 | 0.25 | 1 | 0.5 | 0.5 | 0.5 |
| Streptococcus Group D 9960 | 1 | 0.5 | 0.5 | 0.25 | 0.5 | 0.25 | 1 | 0.5 | 0.5 | 0.5 |
| Haemophilus influenzae Holt | 4 | 2 | 1 | 1 | 2 | 2 | 4 | 2 | 2 | 2 |
| Haemophilus influenzae R252 | 4 | 8 | 4 | 4 | 2 | 2 | 4 | 4 | 2 | 2 |

| Test Organism | 21 | 22 | 23 | 24 | 25 | 26 | 27 | 28 | 29 | 30 |
|---|---|---|---|---|---|---|---|---|---|---|
| Staphylococcus aureus X1.1 | 0.5 | 0.25 | 0.25 | 0.25 | 0.25 | 0.25 | 0.25 | 0.125 | 0.125 | 0.125 |
| Staphylococcus aureus V41 | 0.5 | 0.25 | 0.5 | 0.5 | 0.25 | 0.25 | 0.25 | 0.125 | 0.125 | 0.25 |
| Staphylococcus aureus X400 | 1 | 0.5 | 1 | 0.5 | 0.5 | 0.5 | 0.25 | 0.25 | 0.125 | 0.25 |
| Staphylococcus aureus S13E | 0.5 | 0.25 | 0.5 | 0.25 | 0.25 | 0.25 | 0.25 | 0.125 | 0.125 | 0.25 |
| Staphylococcus epidermidis EPI1 | 0.5 | 0.25 | 0.5 | 0.25 | 0.25 | 0.25 | 0.25 | 0.125 | 0.125 | 0.25 |
| Staphylococcus epidermidis EPI2 | 0.5 | 0.25 | 0.5 | 0.25 | 0.5 | 0.5 | 0.25 | 0.125 | 0.25 | 0.25 |
| Streptococcus pyogenes C203 | 0.5 | 0.25 | 0.5 | 0.5 | NT$^f$ | 0.125 | 0.06 | 0.125 | 0.06 | 0.06 |
| Streptococcus pneumoniae Park I | 0.5 | 0.125 | 0.25 | 0.125 | NT | 0.06 | 0.03 | 0.015 | 0.03 | 0.015 |
| Streptococcus Group D X66 | 0.5 | 0.5 | 1 | 0.5 | 1 | 0.25 | 0.125 | 0.125 | 0.125 | 0.125 |
| Streptococcus Group 9960 | 0.5 | 0.5 | 1 | 0.5 | 0.5 | 0.25 | 0.125 | 0.125 | 0.125 | 0.125 |
| Haemophilus influenzae Holt | 2 | 2 | 8 | 4 | NT | 2 | 1 | 1 | 0.5 | 0.5 |
| Haemophilus influenzae R252 | 8 | 4 | 8 | 4 | NT | 2 | 1 | 1 | 1 | 0.5 |

| Test Organism | 31 | 32 | 33 | 34 | 35 | 36 | 37 | 38 | 39 | 40 |
|---|---|---|---|---|---|---|---|---|---|---|
| Staphylococcus aureus X1.1 | 0.125 | 0.125 | 0.5 | 0.25 | 0.125 | 0.125 | 2 | 0.125 | 0.5 | 0.5 |
| Staphylococcus aureus V41 | 0.125 | 0.25 | 0.5 | 0.25 | 0.125 | 0.25 | 4 | 0.25 | 1 | 1 |
| Staphylococcus aureus X400 | 0.25 | 0.25 | 0.5 | 0.25 | 0.125 | 0.25 | 4 | 0.25 | 1 | 1 |
| Staphylococcus aureus S13E | 0.125 | 0.125 | 0.5 | 0.25 | 0.125 | 0.125 | 2 | 0.125 | 0.5 | 0.5 |
| Staphylococcus epidermidis EPI1 | 0.125 | 0.125 | 0.5 | 0.25 | 0.125 | 0.125 | 2 | 0.25 | 0.5 | 0.5 |
| Staphylococcus epidermidis EPI2 | 0.25 | 0.25 | 0.5 | 0.5 | 0.125 | 0.25 | 4 | 0.25 | 1 | 0.5 |
| Streptococcus pyogenes C203 | 0.125 | 0.06 | 0.25 | 0.06 | 0.06 | 0.06 | 0.5 | 0.06 | 0.125 | 0.125 |
| Streptococcus pneumoniae Park I | 0.03 | 0.03 | 0.125 | 0.015 | 0.03 | 0.03 | 0.5 | 0.03 | 0.03 | 0.06 |
| Streptococcus Group D X66 | 0.125 | 0.125 | 1 | 0.25 | 0.125 | 0.125 | 2 | 0.125 | 0.5 | 0.5 |
| Streptococcus Group D 9960 | 0.125 | 0.125 | 1 | 0.25 | 0.125 | 0.125 | 2 | 0.125 | 0.5 | 0.5 |
| Haemophilus influenzae Holt | NT | NT | 4 | 1 | 1 | 0.5 | NT | NT | 2 | 2 |
| Haemophilus influenzae R252 | NT | NT | 4 | 1 | 1 | 0.5 | NT | NT | 2 | 2 |

| Test Organism | 41 | 42 | 43 | 44 | 45 | 46 | 47 | 48 | 49 | 50 |
|---|---|---|---|---|---|---|---|---|---|---|
| Staphylococcus aureus X1.1 | 0.125 | 0.25 | 0.25 | 0.25 | 1 | 0.25 | 1 | 0.25 | 1 | 1 |
| Staphylococcus aureus V41 | 0.25 | 0.5 | 0.5 | 0.25 | 2 | 0.25 | 2 | 0.25 | 2 | 2 |
| Staphylococcus aureus X400 | 0.5 | 0.5 | 0.5 | 0.25 | 2 | 0.25 | 2 | 0.25 | 4 | 2 |
| Staphylococcus aureus S13E | 0.25 | 0.25 | 0.25 | 0.25 | 1 | 0.25 | 1 | 0.25 | 2 | 1 |
| Staphylococcus epidermidis EPI1 | 0.25 | 0.25 | 0.25 | 0.125 | 0.5 | 0.25 | 1 | 0.25 | 1 | 1 |
| Staphylococcus epidermidis EPI2 | 0.25 | 0.5 | 0.5 | 0.125 | 2 | 0.25 | 2 | 0.25 | 2 | 1 |
| Streptococcus pyogenes C203 | 0.06 | 0.125 | 0.06 | 0.015 | NT | 0.125 | 0.125 | 0.125 | 0.25 | 1 |
| Streptococcus pneumoniae Park I | 0.03 | 0.06 | 0.06 | 0.03 | NT | 0.03 | 0.125 | 0.03 | 0.125 | 0.5 |
| Streptococcus Group D X66 | 0.125 | 0.25 | 0.25 | 0.125 | 1 | 0.25 | 1 | 0.25 | 1 | 1 |
| Streptococcus Group D 9960 | 0.25 | 0.25 | 0.25 | 0.125 | 1 | 0.25 | 1 | 0.25 | 1 | 1 |
| Haemophilus influenzae Holt | NT | NT | NT | NT | NT | 1 | NT | NT | 1 | NT |
| Haemophilus influenzae R252 | NT | NT | NT | NT | NT | 1 | NT | NT | 1 | NT |

| Test Organism | 51 | 52 | 53 | 54 | 55 | 56 | 57 | 58 | 59 | 60 |
|---|---|---|---|---|---|---|---|---|---|---|
| Staphylococcus aureus X1.1 | 1 | 0.5 | 0.25 | 0.125 | 0.125 | 1 | 0.5 | 0.25 | 0.5 | 0.25 |
| Staphylococcus aureus V41 | 1 | 1 | 0.25 | 0.25 | 0.125 | 2 | 0.5 | 0.5 | 0.5 | 0.25 |
| Staphylococcus aureus X400 | 1 | 2 | 0.25 | 0.25 | 0.25 | 2 | 1 | 0.5 | 0.5 | 0.25 |
| Staphylococcus aureus S13E | 0.5 | 1 | 0.25 | 0.125 | 0.25 | 1 | 0.5 | 0.25 | 0.5 | 0.25 |
| Staphylococcus epidermidis EPI1 | 0.5 | 0.5 | 0.25 | 0.125 | 0.25 | 0.5 | 0.5 | 0.25 | 0.5 | 0.25 |
| Staphylococcus epidermidis EPI2 | 1 | 2 | 0.25 | 0.25 | 0.25 | 2 | 1 | 0.5 | 0.5 | 0.5 |
| Streptococcus pyogenes C203 | 0.25 | 0.25 | 0.06 | 0.06 | 0.06 | 0.125 | 0.125 | 0.125 | 0.5 | 0.25 |
| Streptococcus pneumoniae Park I | 0.125 | 0.06 | 0.03 | 0.015 | 0.03 | 0.06 | 0.03 | 0.03 | 0.125 | 0.125 |
| Streptococcus Group D X66 | 1 | 0.5 | 0.25 | 0.125 | 0.125 | 1 | 0.5 | 0.25 | 0.5 | 0.25 |
| Streptococcus Group D 9960 | 1 | 1 | 0.25 | 0.125 | 0.125 | 1 | 0.5 | 0.5 | 0.5 | 0.25 |
| Haemophilus influenzae Holt | NT | 2 | 1 | 0.25 | 1 | 2 | 2 | 2 | 4 | 2 |
| Haemophilus influenzae R252 | NT | 0.5 | 1 | 0.25 | 1 | 2 | 2 | 1 | 2 | 2 |

| Test Organism | 61 | 62 | 63 | 64 | 65 | 66 | 67 | 68 | 69 | 70 |
|---|---|---|---|---|---|---|---|---|---|---|
| Staphylococcus aureus X1.1 | 0.25 | 0.25 | 0.125 | 0.125 | 0.125 | 1 | 0.25 | 0.25 | 1 | 1 |
| Staphylococcus aureus V41 | 0.25 | 0.25 | 0.25 | 0.125 | 0.125 | 2 | 0.25 | 0.25 | 1 | 1 |

TABLE II-continued

Antibiotic Activity of OMT Ester Derivatives

| Test Organism | | | | | | | | | | |
|---|---|---|---|---|---|---|---|---|---|---|
| Staphylococcus aureus X400 | 0.25 | 0.25 | 0.25 | 0.125 | 0.125 | 2 | 0.25 | 0.25 | 1 | 1 |
| Staphylococcus aureus S13E | 0.25 | 0.125 | 0.25 | 0.125 | 0.125 | 1 | 0.25 | 0.25 | 1 | 1 |
| Staphylococcus epidermidis EPI1 | 0.25 | 0.125 | 0.25 | 0.125 | 0.125 | 1 | 0.25 | 0.25 | 1 | 1 |
| Staphylococcus epidermidis EPI2 | 0.25 | 0.25 | 0.25 | 0.25 | 0.125 | 2 | 0.25 | 0.25 | 1 | 1 |
| Streptococcus pyogenes C203 | 0.25 | 0.06 | 0.06 | 0.06 | 0.06 | 0.25 | 0.125 | 0.125 | 1 | 1 |
| Streptococcus pneumoniae Park I | 0.06 | 0.03 | 0.03 | 0.015 | 0.03 | 0.125 | 0.06 | 0.06 | 0.5 | 0.5 |
| Streptococcus Group D X66 | 0.25 | 0.125 | 0.125 | 0.125 | 0.125 | 1 | 0.25 | 0.25 | 2 | 2 |
| Streptococcus Group D 9960 | 0.25 | 0.125 | 0.25 | 0.125 | 0.125 | 2 | 0.25 | 0.25 | 2 | 2 |
| Haemophilus influenzae Holt | 2 | 1 | 1 | 1 | 1 | 2 | 1 | 1 | 8 | 8 |
| Haemophilus influenzae R252 | 2 | 2 | 2 | 1 | 1 | 1 | 1 | 2 | 16 | 16 |

| Test Organism | Test Compound | | | | | | |
|---|---|---|---|---|---|---|---|
| | 71 | 72 | 73 | 74 | 75 | 76 | 77 |
| Staphylococcus aureus X1.1 | 0.25 | 0.125 | 0.25 | 0.25 | 0.125 | 0.125 | 1 |
| Staphylococcus aureus V41 | 0.25 | 0.25 | 0.25 | 0.25 | 0.25 | 0.125 | 2 |
| Staphylococcus aureus X400 | 0.25 | 0.25 | 0.25 | 0.5 | 0.25 | 0.25 | 2 |
| Staphylococcus aureus S13E | 0.25 | 0.25 | 0.25 | 0.25 | 0.125 | 0.125 | 1 |
| Staphylococcus epidermidis EPI1 | 0.25 | 0.25 | 0.25 | 0.25 | 0.125 | 0.125 | 1 |
| Staphylococcus epidermidis EPI2 | 0.25 | 0.25 | 0.25 | 0.25 | 0.125 | 0.125 | 2 |
| Streptococcus pyogenes C203 | 0.25 | 0.125 | 0.25 | 0.25 | 0.125 | 0.06 | 0.25 |
| Streptococcus pneumoniae Park I | 0.03 | 0.03 | 0.03 | 0.03 | 0.03 | 0.015 | 0.25 |
| Streptococcus Group D X66 | 0.25 | 0.25 | 0.25 | 0.5 | 0.25 | 0.25 | 1 |
| Streptococcus Group D 9960 | 0.5 | 0.25 | 0.25 | 0.25 | 0.125 | 0.125 | 1 |
| Haemophilus influenzae Holt | 2 | 2 | 1 | 1 | 0.5 | 0.5 | NT |
| Haemophilus influenzae R252 | 2 | 1 | 2 | 2 | 1 | 1 | 1 |

[a] Compound numbers from Table I
[b] Penicillin-resistant strain
[c] Methicillin-resistant-strain
[d] Ampicillin-sensitive strain
[e] Ampicillin-resistant strain
[f] NT = not tested

TABLE III

Antibiotic Activity of OMT Ester Derivatives

| Test Organism | Test Compound[a] | | | | | | | | | |
|---|---|---|---|---|---|---|---|---|---|---|
| | 1 | 2 | 3 | 4 | 5 | 6 | 7 | 8 | 9 | 10 |
| Staphylococcus aureus | 1.56 | 3.12 | 1.56 | 1.56 | 6.25 | 0.39 | 0.78 | 0.39 | 0.78 | 0.39 |
| Streptococcus sp. 80 | 0.78 | <0.78 | <0.78 | <0.78 | 3.12 | 0.195 | 0.195 | 0.195 | 0.195 | 0.195 |
| Pasteurella multocida 17E[b] | 1.56 | 3.12 | 3.12 | 3.12 | 50 | 1.56 | 3.12 | 1.56 | 1.56 | 1.56 |
| Pasteurella multocida 60A[c] | 1.56 | 1.56 | 3.12 | 3.12 | 50 | 0.78 | 3.12 | 1.56 | 1.56 | 1.56 |
| Pasteurella multocida 22A | 3.12 | 3.12 | 3.12 | 3.12 | >50 | 1.56 | 3.12 | 3.12 | 6.25 | 6.25 |
| Pasteurella multocida 40G | 6.25 | 6.25 | 6.25 | 6.25 | 50 | NT[d] | 1.56 | 1.56 | 1.56 | 1.56 |
| Pasteurella multocida 68C | 3.12 | 3.12 | 1.56 | 1.56 | 25 | 0.78 | 1.56 | 1.56 | 3.12 | 1.56 |
| Pasteurella haemolytica 22C | 12.5 | 12.5 | 12.5 | 6.25 | >50 | 6.25 | 6.25 | 3.12 | 3.12 | 6.25 |
| Pasteurella haemolytica 41D | 12.5 | 12.5 | 6.25 | 12.5 | >50 | 3.12 | 6.25 | 3.12 | 3.12 | 6.25 |
| Pasteurella haemolytica 23C | 12.5 | 12.5 | 6.25 | 6.25 | >50 | 3.12 | 6.25 | 6.25 | 3.12 | 6.25 |
| Mycoplasma gallisepticum | 0.39 | 0.39 | 0.78 | 0.39 | 12.5 | <0.05 | 0.39 | 0.048 | <0.78 | 0.097 |
| Mycoplasma synoviae | 0.39 | 0.78 | 0.195 | 0.78 | 12.5 | 0.39 | 0.39 | 0.048 | 0.097 | 0.097 |
| Mycoplasma hyorhinis | 3.12 | 3.12 | 3.12 | 1.56 | 50 | 0.39 | 3.12 | 0.78 | 1.56 | 0.78 |

[a] Compound numbers from Table I.
[b] Bovine isolate.
[c] Avian isolate.
[d] NT = not tested.

| Test Organism | Test Compound | | | | | | | | | |
|---|---|---|---|---|---|---|---|---|---|---|
| | 11 | 12 | 13 | 14 | 15 | 16 | 17 | 18 | 19 | 20 |
| Staphylococcus aureus | 6.25 | 0.39 | 0.39 | 0.39 | 0.39 | 0.39 | 0.195 | 0.78 | 0.39 | 0.39 |
| Streptococcus sp. 80 | 1.56 | 0.39 | 0.195 | 0.195 | 0.097 | 0.195 | <0.05 | 0.195 | <0.05 | 0.39 |
| Pasteurella multocida 17E | 25 | 1.56 | 1.56 | 1.56 | 1.56 | 1.56 | 1.56 | 1.56 | 1.56 | 1.56 |
| Pasteurella multocida 60A | 50 | 1.56 | 1.56 | 0.78 | 1.56 | 3.12 | 3.12 | 3.12 | 3.12 | 3.12 |
| Pasteurella multocida 22A | NT | 0.78 | 1.56 | 3.12 | NT | NT | NT | NT | NT | NT |
| Pasteurella multocida 40G | NT | 0.78 | 3.12 | 1.56 | NT | NT | NT | NT | NT | NT |
| Pasteurella multocida 68C | NT | 1.56 | 1.56 | 1.56 | NT | NT | NT | NT | NT | NT |
| Pasteurella haemolytica 22C | NT | 6.25 | 3.12 | 6.25 | NT | NT | NT | NT | NT | NT |
| Pasteurella haemolytica 41D | NT | 3.12 | 6.25 | 6.25 | NT | NT | NT | NT | NT | NT |
| Pasteurella haemolytica 23C | NT | 3.12 | 3.12 | 3.12 | NT | NT | NT | NT | NT | NT |
| Mycoplasma gallisepticum | 0.39 | <0.05 | 0.05 | 0.05 | <0.05 | <0.05 | <0.05 | <0.05 | <0.05 | <0.05 |
| Mycoplasma synoviae | 0.39 | <0.05 | 0.097 | 0.05 | <0.05 | 0.097 | <0.05 | <0.05 | <0.05 | <0.05 |
| Mycoplasma hyorhinis | 12.5 | 3.12 | 0.78 | 6.25 | 0.78 | 0.78 | 0.39 | 0.39 | 6.25 | 3.12 |

| Test Organism | Test Compound | | | | | | | | | |
|---|---|---|---|---|---|---|---|---|---|---|
| | 21 | 22 | 23 | 24 | 25 | 26 | 27 | 28 | 29 | 30 |
| Staphylococcus aureus | 0.39 | 0.78 | 0.78 | 0.78 | 0.097 | 0.39 | 0.097 | 0.195 | 0.097 | 0.195 |
| Streptococcus sp. 80 | 0.195 | 0.097 | 0.39 | 0.39 | 0.195 | 0.195 | 0.05 | <0.05 | 0.05 | <0.05 |
| Pasteurella multocida 17E | 1.56 | 1.56 | 6.25 | 6.25 | 6.25 | 1.56 | 1.56 | 1.56 | 1.56 | 1.56 |
| Pasteurella multocida 60A | 1.56 | 3.12 | 6.25 | 6.25 | 6.25 | 0.78 | 0.78 | 0.78 | 0.78 | 1.56 |
| Pasteurella multocida 22A | NT | NT | NT | NT | 25 | 1.56 | 3.12 | 3.12 | 1.56 | 1.56 |
| Pasteurella multocida 40G | NT | NT | NT | NT | NT | NT | 3.12 | NT | 1.56 | 0.78 |

TABLE III-continued
Antibiotic Activity of OMT Ester Derivatives

| Test Organism | | | | | | | | | | |
|---|---|---|---|---|---|---|---|---|---|---|
| Pasteurella multocida 68C | NT | NT | NT | NT | 6.25 | 1.56 | 1.56 | 0.78 | 1.56 | 0.78 |
| Pasteurella haemolytica 22C | NT | NT | NT | NT | 12.5 | 6.25 | 3.12 | 6.25 | 3.12 | 3.12 |
| Pasteurella haemolytica 41D | NT | NT | NT | NT | 12.5 | 6.25 | 3.12 | 3.12 | 3.12 | 3.12 |
| Pasteurella haemolytica 23C | NT | NT | NT | NT | 12.5 | 3.12 | 3.12 | 3.12 | 3.12 | 3.12 |
| Mycoplasma gallisepticum | <0.05 | <0.05 | 0.097 | <0.05 | <0.05 | <0.05 | 0.05 | <0.05 | 0.05 | <0.05 |
| Mycoplasma synoviae | <0.05 | <0.05 | 0.39 | 0.097 | 1.56 | 0.39 | 0.05 | <0.05 | 0.05 | NT |
| Mycoplasma hyorhinis | 0.78 | 0.78 | 3.12 | 6.25 | 0.78 | 0.39 | 0.097 | 1.56 | 0.195 | 0.195 |

| | Test Compound | | | | | | | | | |
|---|---|---|---|---|---|---|---|---|---|---|
| Test Organism | 31 | 32 | 33 | 34 | 35 | 36 | 37 | 38 | 39 | 40 |
| Staphylococcus aureus | <0.05 | 0.097 | 0.39 | 0.097 | 0.39 | 0.39 | 0.39 | <0.05 | 1.56 | 0.78 |
| Streptococcus sp. 80 | <0.05 | 0.097 | 0.39 | <0.05 | 0.097 | <0.05 | <0.05 | <0.05 | 0.195 | 0.195 |
| Pasteurella multocida 17E | 1.56 | 1.56 | 3.12 | 1.56 | 1.56 | 1.56 | 1.56 | 1.56 | 6.25 | 6.25 |
| Pasteurella multocida 60A | 0.78 | 0.78 | 3.12 | 1.56 | 1.56 | 1.56 | 3.12 | 1.56 | 12.5 | 6.25 |
| Pasteurella multocida 22A | 1.56 | 0.78 | 3.12 | 3.12 | 6.25 | 3.12 | 6.25 | 3.12 | 25 | 12.5 |
| Pasteurella multocida 40G | 1.56 | 1.56 | 3.12 | 1.56 | 3.12 | 1.56 | 3.12 | 1.56 | 6.25 | 6.25 |
| Pasteurella multocida 68C | 0.78 | 0.39 | 3.12 | 1.56 | 1.56 | 0.78 | 0.78 | 1.56 | 12.5 | 6.25 |
| Pasteurella haemolytica 22C | 1.56 | 1.56 | 12.5 | 3.12 | 3.12 | 3.12 | 6.25 | 3.12 | 12.5 | 12.5 |
| Pasteurella haemolytica 41D | 3.12 | 3.12 | 12.5 | 3.12 | 1.56 | 3.12 | 12.5 | 6.25 | 12.5 | 12.5 |
| Pasteurella haemolytica 23C | 1.56 | 3.12 | 12.5 | 3.12 | 3.12 | 3.12 | 6.25 | 6.25 | 12.5 | 12.5 |
| Mycoplasma gallisepticum | <0.05 | <0.05 | 0.05 | <0.05 | <0.05 | <0.05 | <0.05 | <0.05 | <0.05 | <0.05 |
| Mycoplasma synoviae | <0.05 | <0.05 | 0.39 | NT | 0.097 | NT | 0.78 | 0.097 | NT | NT |
| Mycoplasma hyorhinis | 3.12 | 3.12 | 0.78 | 3.12 | 3.12 | 1.56 | 6.25 | 3.12 | 1.56 | 0.39 |

| | Test Compound | | | | | | | | | |
|---|---|---|---|---|---|---|---|---|---|---|
| Test Organism | 41 | 42 | 43 | 44 | 45 | 46 | 47 | 48 | 49 | 50 |
| Staphylococcus aureus | 0.78 | 0.78 | 0.39 | 0.39 | 0.78 | 0.195 | 0.78 | 0.39 | 3.12 | 0.39 |
| Streptococcus sp. 80 | 0.195 | 0.39 | 0.195 | 0.39 | 0.195 | 0.097 | <0.05 | 0.195 | 0.39 | 0.39 |
| Pasteurella multocida 17E | 3.12 | 6.25 | 3.12 | 3.12 | 3.12 | 3.12 | 6.25 | 6.25 | 3.12 | 12.5 |
| Pasteurella multocida 60A | 3.12 | 3.12 | 3.12 | 0.78 | 1.56 | 1.56 | 3.12 | 6.25 | 3.12 | 6.25 |
| Pasteurella multocida 22A | 3.12 | 6.25 | 3.12 | 3.12 | 3.12 | 6.25 | 12.5 | 6.25 | 6.25 | 25 |
| Pasteurella multocida 40G | 3.12 | 1.56 | 3.12 | 3.12 | NT | 6.25 | 12.5 | 6.25 | 3.12 | 3.12 |
| Pasteurella multocida 68C | 3.12 | 3.12 | 1.56 | 3.12 | 1.56 | 3.12 | 3.12 | 6.25 | 25 | 6.25 |
| Pasteurella haemolytica 22C | 6.25 | 6.25 | 6.25 | 3.12 | 6.25 | 3.12 | 12.5 | 6.25 | 12.5 | 25 |
| Pasteurella haemolytica 41D | 6.25 | 3.12 | 3.12 | 6.25 | 3.12 | 3.12 | 12.5 | 6.25 | 12.5 | 25 |
| Pasteurella haemolytica 23C | 6.25 | 6.25 | 6.25 | 6.25 | 3.12 | 3.12 | 12.5 | 12.5 | 12.5 | 25 |
| Mycoplasma gallisepticum | 0.195 | 0.39 | 0.78 | 0.78 | 0.39 | 0.05 | 0.195 | 0.78 | 1.56 | 0.195 |
| Mycoplasma synoviae | 0.39 | 0.195 | <0.05 | <0.05 | 0.39 | 0.097 | 1.56 | 0.78 | 0.78 | 1.56 |
| Mycoplasma hyorhinis | 12.5 | 12.5 | 0.78 | 0.78 | 3.12 | 0.78 | 12.5 | 0.78 | 6.25 | 6.25 |

| | Test Compound | | | | | | | | | |
|---|---|---|---|---|---|---|---|---|---|---|
| Test Organism | 51 | 52 | 53 | 54 | 55 | 56 | 57 | 58 | 59 | 60 |
| Staphylococcus aureus | 0.78 | 1.56 | 0.195 | 0.195 | 0.195 | 0.78 | 3.12 | 1.56 | 0.78 | 0.39 |
| Streptococcus sp. 80 | 0.78 | 0.78 | <0.05 | 0.195 | 0.05 | 0.195 | 0.39 | 0.78 | 0.39 | 0.39 |
| Pasteurella multocida 17E | 3.12 | 3.12 | 1.56 | 0.78 | 3.12 | 3.12 | 6.25 | 3.12 | 3.12 | 3.12 |
| Pasteurella multocida 60A | 3.12 | 1.56 | 1.56 | 1.56 | 3.12 | 3.12 | 3.12 | 3.12 | 3.12 | 3.12 |
| Pasteurella multocida 22A | 6.25 | 3.12 | 1.56 | 6.25 | 6.25 | 6.25 | 3.12 | 6.25 | 12.5 | 3.12 |
| Pasteurella multocida 40G | 3.12 | 3.12 | 1.56 | 3.12 | 6.25 | 6.25 | 3.12 | 3.12 | 3.12 | 12.5 |
| Pasteurella multocida 68C | 3.12 | 6.25 | 0.78 | 0.78 | 3.12 | 3.12 | 3.12 | 1.56 | 3.12 | 1.56 |
| Pasteurella haemolytica 22C | 3.12 | 25 | 3.12 | 3.12 | 3.12 | 6.25 | 6.25 | 12.5 | 12.5 | 6.25 |
| Pasteurella haemolytica 41D | 3.12 | 6.25 | 3.12 | 3.12 | 6.25 | 6.25 | 6.25 | 6.25 | 6.25 | 6.25 |
| Pasteurella haemolytica 23C | 3.12 | 12.5 | 3.12 | 3.12 | 3.12 | 6.25 | 6.25 | 6.25 | 6.25 | 6.25 |
| Mycoplasma gallisepticum | <0.05 | 3.12 | <0.05 | 0.097 | 0.05 | 0.39 | 0.195 | <0.05 | 0.39 | <0.05 |
| Mycoplasma synoviae | 0.78 | 1.56 | <0.05 | NT | 0.05 | 0.78 | 0.39 | 0.78 | 1.56 | 0.78 |
| Mycoplasma hyorhinis | 6.25 | 3.12 | 3.12 | 0.78 | 0.78 | 12.5 | 6.25 | 6.25 | 6.25 | 6.25 |

| | Test Compound | | | | | | | | | |
|---|---|---|---|---|---|---|---|---|---|---|
| Test Organism | 61 | 62 | 63 | 64 | 65 | 66 | 67 | 68 | 69 | 70 |
| Staphylococcus aureus | 1.56 | 0.78 | 1.56 | 0.78 | 0.39 | 3.12 | 1.56 | 1.56 | 6.25 | 6.25 |
| Streptococcus sp. 80 | 1.56 | 0.195 | 0.195 | <0.05 | 0.195 | <0.78 | <0.78 | <0.78 | 1.56 | 1.56 |
| Pasteurella multocida 17E | 6.25 | 3.12 | 6.25 | 1.56 | 3.12 | 3.12 | 3.12 | 3.12 | 12.5 | 12.5 |
| Pasteurella multocida 60A | 3.12 | 12.5 | 3.12 | 1.56 | 3.12 | 6.25 | 3.12 | 3.12 | 12.5 | 25 |
| Pasteurella multocida 22A | 6.25 | 3.12 | 6.25 | 1.56 | 3.12 | 3.12 | 3.12 | 3.12 | 12.5 | 12.5 |
| Pasteurella multocida 40G | 6.25 | 3.12 | 3.12 | 1.56 | 1.56 | 3.12 | 3.12 | 3.12 | 12.5 | 12.5 |
| Pasteurella multocida 68C | 6.25 | 6.25 | 6.25 | 1.56 | 3.12 | 3.12 | 1.56 | 1.56 | 12.5 | 12.5 |
| Pasteurella haemolytica 22C | 12.5 | 6.25 | 6.25 | 3.12 | 3.12 | 25 | 12.5 | 6.25 | 25 | 25 |
| Pasteurella haemolytica 41D | 6.25 | 3.12 | 12.5 | 3.12 | 3.12 | 25 | 6.25 | 6.25 | 25 | 25 |
| Pasteurella haemolytica 23C | 12.5 | 6.25 | 6.25 | 3.12 | 3.12 | 12.5 | 6.25 | 3.12 | 25 | 25 |
| Mycoplasma gallisepticum | 0.78 | <0.05 | 0.39 | 0.097 | 0.195 | 1.56 | <0.048 | 0.097 | 0.78 | 1.56 |
| Mycoplasma synoviae | 1.56 | <0.05 | <0.05 | <0.05 | <0.05 | 1.56 | <0.048 | <0.048 | 1.56 | 0.39 |
| Mycoplasma hyorhinis | 6.25 | 0.78 | 1.56 | 0.78 | 0.78 | 6.25 | 0.39 | 0.097 | 3.12 | 3.12 |

| | Test Compound | | | | | | |
|---|---|---|---|---|---|---|---|
| Test Organism | 71 | 72 | 73 | 74 | 75 | 76 | 77 |
| Staphylococcus aureus | 0.78 | 1.56 | 0.78 | 1.56 | 0.78 | 0.39 | 1.56 |
| Streptococcus sp. 80 | 1.56 | 1.56 | 0.39 | 0.39 | 0.39 | 0.39 | 0.78 |
| Pasteurella multocida 17E | 6.25 | 6.25 | 6.25 | 1.56 | 6.25 | 6.25 | 3.12 |
| Pasteurella multocida 60A | 6.25 | 3.12 | 6.25 | 1.56 | 6.25 | 6.25 | 3.12 |
| Pasteurella multocida 22A | 3.12 | 3.12 | >50 | 25 | >50 | >50 | 50 |
| Pasteurella multocida 40G | 3.12 | 3.12 | 6.25 | 12.5 | 12.5 | 6.25 | 25 |

TABLE III-continued

| Antibiotic Activity of OMT Ester Derivatives | | | | | | | |
|---|---|---|---|---|---|---|---|
| Pasteurella multocida 68C | 6.25 | 3.12 | 3.12 | 12.5 | 3.12 | 3.12 | 25 |
| Pasteurella haemolytica 22C | 50 | 12.5 | 6.25 | 6.25 | 6.25 | 6.25 | 12.5 |
| Pasteurella haemolytica 41D | 12.5 | 12.5 | 3.12 | 1.56 | 6.25 | 3.12 | 12.5 |
| Pasteurella haemolytica 23C | 12.5 | 6.25 | 6.25 | 3.12 | 3.12 | 3.12 | 12.5 |
| Mycoplasma gallisepticum | 0.195 | 0.195 | 0.097 | <0.048 | 0.048 | 0.097 | 0.78 |
| Mycoplasma synoviae | 0.78 | 0.78 | 0.097 | 0.195 | <0.048 | <0.048 | 0.78 |
| Mycoplasma hyorhinis | 12.5 | 25 | 0.39 | 0.78 | 0.78 | 0.78 | 3.12 |

The OMT ester derivatives of this invention have shown in vivo antimicrobial activity against experimental bacterial infections caused by gram-positive bacteria. When two doses of test compound were administered to mice with experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed for illustrative compounds are given in Table IV.

TABLE IV $ED_{50}$ Values of OMT Ester Derivatives[a]

| | *Streptococcus pyogenes* C203 | |
|---|---|---|
| Test Compound[b] | Subcutaneous | Oral |
| 1 | 6.8 | >150 |
| 3 | >15 | 139 |
| 4 | 5.7 | 167 |
| 6 | >30 | 146 |
| 7 | >15 | 100 |
| 9 | 6.4 | 137 |
| 11 | 5.3 | >150 |
| 12 | 8.1 | 150 |
| 13 | 3.3 | 109 |
| 14 | 6.0 | 106 |
| 22 | 7.5 | >150 |
| 26 | 10.6 | 136 |
| 27 | >30 | 159 |
| 28 | 6.5 | 155 |
| 29 | 5.0 | >100 |
| 33 | 9.7 | 146 |
| 36 | 6.0 | >150 |
| 37 | NT[c] | >150 |
| 38 | NT | >150 |
| 40 | 5.0 | 116 |
| 42 | 11 | >150 |
| 44 | 13 | 150 |
| 46 | 15 | 146 |
| 48 | >30 | >150 |
| 49 | >30 | >100 |
| 52 | 2.1 | 92 |
| 57 | 2.6 | 91 |
| 68 | 3.8 | >100 |
| 72 | 2.3 | 87 |
| 74 | 3.0 | >100 |
| 76 | 25 | >100 |

[a] mg/kg × 2; doses given 1 and 4 hours post-infection
[b] Compound numbers from Table I
[c] Not Tested Certain OMT ester derivatives are active in vivo against Pasteurella infections. Table V summarizes the results of tests in which the ester derivatives were administered to one-day-old chicks at a dosage level of 30 mg/kg by subcutaneous injection one and four hours post challenge of the chicks with *Pasteurella multocida* (0.1 ml of a $10^{-3}$ dilution of a 20-hour tryptose broth culture of avian *P. multocida* given subcutaneously). All nonmedicated infected chicks (ten in each control group) died within 24 hours of Pasteurella challenge.

TABLE V

Treatment of Pasteurella Infections in Chicks

| Compound[a] | Deaths in Treated Chicks/Number Treated |
|---|---|
| 1 | 0/10 |
| 3 | 0/10 |
| 6 | 8/10 |
| 7 | 5/10 |
| 8 | 6/10 |
| 9 | 0/10 |
| 10 | 1/10 |
| 12 | 0/10 |
| 13 | 0/10 |
| 14 | 0/10 |
| 15 | 10/10 |
| 16 | 6/10 |
| 17 | 10/10 |
| 18 | 0/10 |
| 19 | 10/10 |
| 20 | 0/10 |
| 21 | 10/10 |
| 22 | 1/10 |
| 23 | 10/10 |
| 24 | 1/10 |
| 25 | 10/10 |
| 26 | 10/10 |
| 27 | 9/10 |
| 28 | 8/10 |
| 29 | 0/10 |
| 30 | 6/10 |
| 31 | 10/10 |
| 32 | 2/10 |
| 33 | 8/10 |
| 34 | 9/10 |
| 35 | 1/10 |
| 36 | 1/10 |
| 37 | 10/10 |
| 38 | 1/10 |
| 39 | 10/10 |
| 40 | 10/10 |
| 41 | 10/10 |
| 42 | 0/10 |
| 43 | 8/10 |
| 44 | 0/10 |
| 45 | 10/10 |
| 46 | 8/10 |
| 47 | 9/10 |
| 48 | 10/10 |
| 49 | 10/10 |
| 54 | 0/10 |
| 55 | 10/10 |
| 56 | 10/10 |
| 57 | 0/10 |
| 63 | 15/20 |
| 65 | 11/15 |
| 67 | 8/10 |
| 68 | 0/10 |
| 71 | 6/10 |
| 72 | 5/10 |
| 73 | 0/10 |
| 74 | 0/10 |
| 75 | 10/10 |
| 76 | 10/10 |

[a] Compound numbers from Table I

This invention also relates, therefore, to methods of controlling gram-positive and Pasteurella infections. In carrying out the methods of this invention, an effective amount of a compound of formula 1 is administered parenterally to an infected or susceptible warm-blooded animal. The dose which is effective to control gram-positive and/or Pasteurella infections will vary with the severity of the infection and the age, weight, and condition of the animal. The total dose required for protection will generally, however, be in the range of from about 1 to about 200 mg/kg and preferably will be in the range of from about 5 to about 100 mg/kg. Suitable dosage regimens can be constructed.

In another aspect, this invention relates to compositions useful for the control of gram-positive and/or Pasteurella infections. These compositions comprise a compound of formula 1 together with a suitable pharmaceutical vehicle. Such compositions may be formulated for parenteral administration by methods recognized in the pharmaceutical art. Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided:

PREPARATION 1

Preparation of OMT from DMT

A. Shake-flask Fermentation of DMT

A lyophilized pellet of *Streptomyces fradiae* NRRL 12170 is dispersed in 1–2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12170, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMT

In order to provide a larger volume of inoculum, 1200 ml of incubated vegetative medium, prepared in a manner similar to that described in section A, is used to inoculate 250 gallons of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 350-gallon tank for about 48 hours at 28° C., with adequate aeration and agitation.

Incubated second-stage medium (144 gallons) thus prepared is used to inoculate 1000 gallons of sterile production medium having the following composition:

| Ingredient | Amount (%) |
| --- | --- |
| Fish meal | 0.875 |
| Corn meal | 1.5 |
| Corn gluten | 0.875 |
| CaCO$_3$ | 0.2 |
| NaCl | 0.1 |
| (NH$_4$)$_2$HPO$_4$ | 0.04 |
| Beet molasses | 2.0 |
| Soybean oil (crude) | 3.0 |
| Lecithin | 0.09 |
| Water | 91.32 |

| -continued | |
|---|---|
| Ingredient | Amount (%) |
| Adjust pH to 7.2 with 50% NaOH solution. | |

The inoculated production medium is allowed to ferment in a 1600-gallon tank for 8 to 9 days at a temperature of 28° C. The fermentation medium is aerated with sterile air to keep the dissolved oxygen level between about 30% and 50% and is stirred with conventional agitators at about 250 rpm.

C. Isolation of DMT

Harvested whole broth (3800 L), obtained as described in Section B, is filtered, using a filter aid. The mycelial cake is washed with water; this water wash is added to the filtrate.

The pH of the filtrate is adjusted to pH 9.2, using a 50% aqueous solution of sodium hydroxide (9.5 L). The filtrate is extracted with ethyl acetate (2000 L). Deionized water (450 L) and sodium phosphate monobasic (6.4 kg) are added to the ethyl acetate extract with thorough mixing. The pH of this mixture is adjusted from about pH 6.0 to pH 4.35, using a phosphoric acid solution (3300 ml; 2 parts water to one part phosphoric acid). The aqueous phase is separated. The pH of the enriched aqueous phase is adjusted to pH 6.5 using a 50% aqueous sodium hydroxide solution (700 ml).

The resulting solution is concentrated to a volume of about 225 L under vacuum. The pH of the concentrated solution is adjusted to pH 9.2 by the addition of 10% aqueous sodium hydroxide (16 L). The resulting basic solution is permitted to stand overnight. The crystals which form are separated by filtration, washed with deionized water (50 L), and dried to give about 8.6 kg of product. The product thus obtained can be recrystallized from acetone-water.

D. Preparation of OMT

DMT, prepared as described in Section C, is dissolved in a dilute hydrochloric acid solution (final pH 1.8). The resulting solution is allowed to stand for 24 hours at room temperature and then is adjusted to pH 9.0 by the addition of sodium hydroxide. This basic solution is extracted with ethyl acetate, dichloromethane or chloroform. The extract is evaporated under vacuum to give OMT.

PREPARATION 2

Alternate Preparation of OMT from DMT

OMT is prepared from DMT by treating the DMT in the fermentation broth in which it is produced with mild acid as described in Section D of Preparation 1. Isolation of the OMT is accomplished by a procedure similar to that described for DMT in Section C of Preparation 1.

PREPARATION 3

N-(Phenoxyacetyloxy)succinimide

A suspension of phenoxyacetic acid (15.2 g, 100 mmol) and N-hydroxysuccinimide (11.5 g, 100 mmol) in ethyl acetate (300 ml) was cooled in an ice bath, treated with N,N'-dicyclohexylcarbodiimide (20.6 g, 100 mmol) and stirred for 1 hour at 0° and then overnight at room temperature. The precipitate which formed was filtered; the filtrate was evaporated to dryness; and the residue was crystallized from ethyl acetate to yield 15.0 g of N-(phenoxyacetyloxy)succinimide.

TLC Analysis

TLC analysis is conveniently carried out on silica gel, using an appropriate solvent system such as dichloromethane:methanol:conc. ammonium hydroxide (90:10:2) and UV light, anisaldehyde spray or iodine for detection.

EXAMPLE 1

2',4'-Di-O-acetyl-OMT (Compound 3)

OMT (50 g) was dissolved in acetone (900 ml) and treated dropwise with stirring at room temperature with acetic anhydride (25 ml). After 2 hours, solvent was evaporated under reduced pressure; the concentrate was diluted with toluene (200 ml) and re-evaporated. The residue was dissolved in dichloromethane, and this solution was extracted with saturated NaHCO$_3$ solution. The organic layer was separated, dried (Na$_2$SO$_4$), filtered and evaporated to dryness. The glassy residue was chromatographed on silica gel (Waters Prep 500), eluting first with a linear gradient of 3:1 toluene-ethyl acetate (4 liters) and ethyl acetate (4 liters) and then with ethyl acetate (2 liters). Fractions containing the desired product were located by TLC analysis, combined and evaporated to dryness to yield 42.0 g (74%) of 2',4'-di-O-acetyl-OMT (3).

EXAMPLE 2

2',4',23-Tri-O-acetyl-OMT (Compound 7)

OMT (15 g, 25.1 mmol) was dissolved in anhydrous pyridine (300 ml), cooled in an ice bath and treated with acetic anhydride (7.8 ml) with stirring at 0° C. The reaction was stirred overnight with exclusion of moisture while warming to room temperature. Solvent was evaporated under reduced pressure; the residue was dissolved in dichloromethane, extracted with saturated NaHCO$_3$ solution, dried (Na$_2$SO$_4$) and filtered. The filtrate was evaporated under reduced pressure. The residue was chromatographed on silica gel (Waters Prep 500), eluting with a linear gradient of 1:1 toluene-ethyl acetate (4 liters) and ethyl acetate (4 liters). Fractions containing the desired product were located by TLC analysis, combined and evaporated to dryness to yield 10.0 g of 2',4',23-tri-O-acetyl-OMT (7).

EXAMPLE 3

2',4'-Di-O-acetyl-23-O-i-valeryl-OMT (Compound 21)

2',4'-Di-O-acetyl-OMT (2.5 g, 3.7 mmol), prepared as described in Example 1, was dissolved in dichloromethane (50 ml) and pyridine (0.75 ml), cooled in an ice bath and treated with a solution of isovaleryl chloride (0.50 ml, 4.1 mmol) in dichloromethane (10 ml), added dropwise over a 30-minute period. After stirring for 2 hours, additional pyridine (0.7 ml) and isovaleryl chloride (0.2 ml) in dichloromethane (5 ml) were added; after 3 hours, further pyridine (0.6 ml) and isovaleryl chloride (0.2 ml) in dichloromethane (5 ml) were added to consume starting material. After a total of 4.5 hours, the mixture was poured into saturated NaHCO$_3$ solution, and the product was extracted into dichloromethane. The organic layer was separated, dried (Na$_2$SO$_4$) and filtered. The filtrate was evaporated under reduced pressure. The residue was purified by flash chromatography on silica gel, eluting with ethyl acetate. Fractions containing the desired product were located by TLC analysis, combined and evaporated to dryness to yield 2.35 g of 2',4'-di-O-acetyl-23-O-i-valeryl-OMT (21).

EXAMPLE 4

2',4'-Di-O-acetyl-23-O-dichloroacetyl-OMT (Compound 66)

2',4'-Di-O-acetyl-OMT (5.0 g, 7.34 mmol), prepared as described in Example 1, was dissolved in dichloromethane (100 ml) and pyridine (1 ml), cooled in an ice bath and treated with dichloroacetyl chloride (0.85 ml, 8.8 mmol). The mixture was stirred for 1.5 hours while allowing the ice bath to melt. The mixture was then poured into saturated $NaHCO_3$ solution, and the product was extracted into dichloromethane. The organic layer was separated, dried ($Na_2SO_4$) and filtered. The filtrate was evaporated under reduced pressure. The residue was dissolved in dichloromethanecyclohexane and re-evaporated until a solid product was obtained. The solid was suspended in hexane, filtered, washed with hexane and air-dried to yield 5.2 g (89%) of 2',4'-di-O-acetyl-23-O-dichloroacetyl-OMT (66).

EXAMPLE 5

2',4'-Di-O-acetyl-23-O-phenylacetyl-OMT (Compound 27)

2',4'-Di-O-acetyl-OMT (6.81 g, 10.0 mmol), prepared as described in Example 1, was dissolved in dichloromethane (100 ml) and pyridine (5 ml), cooled in an ice bath and treated with a solution of phenylacetyl chloride (1.70 g, 11.0 mmol) in dichloromethane (15 ml) while excluding moisture. An additional amount of phenylacetyl chloride (0.14 ml, 1 mmol) in dichloromethane (5 ml) was added after 2 and after 3 hours in order to consume unreacted starting material (based on TLC analysis). After 4 hours, the reaction mixture was poured into saturated $NaHCO_3$ solution. The organic layer was separated, dried ($Na_2SO_4$), filtered and evaporated under reduced pressure. The residue was dissolved in a small volume of toluene and purified by flash chromatography on silica gel (E. Merck 60). The column was eluted stepwise with 4:1 toluene-ethyl acetate (400 ml), 3:1 toluene-ethyl acetate (300 ml), 2:1 toluene-ethyl acetate (300 ml) and 1:1 toluene-ethyl acetate (1200 ml). Fractions containing the desired product were located by TLC analysis, combined and evaporated to dryness to give 5.8 g (72%) of 2',4'-di-O-acetyl-23-O-phenylacetyl-OMT (27).

EXAMPLE 6

23-O-Benzoyl-2',4'-Di-O-acetyl-OMT (Compound 6)

2',4'-Di-O-acetyl-OMT (2.39 g, 3.5 mmol), prepared as described in Example 1, was dissolved in pyridine (50 ml), cooled in an ice bath and treated with benzoic anhydride (870 mg, 3.8 mmol) in dichloromethane (2 ml). After stirring overnight at room temperature, additional benzoic anhydride (870 mg) was added to consume starting material. After stirring for another 5 hours at room temperature, the mixture was diluted with toluene and evaporated to dryness under reduced pressure. The residue was dissolved in dichloromethane, extracted with saturated $NaHCO_3$ solution, dried ($Na_2SO_4$) and filtered. The filtrate was evaporated to drynesss. The residue was dissolved in toluene and purified by flash chromatography on silica gel. The column was eluted stepwise with mixtures of toluene-ethyl acetate (500 ml of 4:1, 450 ml of 3:2, 450 ml of 8:7 and 450 ml of 1:1). Fractions containing the desired product were located by TLC analysis, combined and evaporated to dryness to yield 850 mg of 23-O-benzoyl-2',4'-di-O-acetyl-OMT (6).

EXAMPLE 7

2',4'-Di-O-acetyl-23-O-phenoxyacetyl-OMT (Compound 34)

2',4'-Di-O-acetyl-OMT (5.0 g, 7.35 mmol), prepared as described in Example 1, was dissolved in dichloromethane (200 ml), treated with N-(phenoxyacetyloxy)-succinimide (4.5 g, 18 mmol), prepared as described in Preparation 3, and pyridine (25 ml) and stirred overnight at room temperature excluding moisture. The mixture was then treated with methanol (15 ml) for 2 hours to decompose excess acylating agent. The mixture was concentrated under reduced pressure, diluted with toluene and evaporated. The residual oil was dissolved in toluene and chromatographed on silica gel (Waters Prep 500), eluting with a linear gradient of 3:1 toluene-ethyl acetate (4 liters) and ethyl acetate (4 liters). Fractions containing the desired product were located by TLC analysis, combined and evaporated to dryness to yield 3.7 g (67%) of 2',4'-di-O-acetyl-23-O-phenoxyacetyl-OMT (34).

EXAMPLE 8

2',4'-Di-O-acetyl-23-O-[(3,4-dichlorophenylthio)acetyl]-OMT (Compound 37)

(3,4-Dichlorophenylthio)acetic acid (6.96 g, 29.4 mmol) and N-hydroxysuccinimide (3.38 g, 29.4 mmol) were dissolved in dichloromethane (200 ml) and treated with N,N'-dicyclohexylcarbodiimide (6.05 g, 29.4 mmol) while stirring at room temperature. After 15 minutes, 2',4'-di-O-acetyl-OMT (4.0 g, 4.9 mmol) and then pyridine (25 ml) were added. After stirring for 1.5 days at room temperature, the precipitate was separated by filtration and extracted with dichloromethane. The filtrates were combined, washed with saturated $NaHCO_3$ solution, and concentrated under reduced pressure (50 ml). The concentrate was treated with methanol (15 ml) for 1 hour at room temperature to decompose the unreacted acylating agent. Solvent was evaporated under reduced pressure, and the residual oil was triturated with hexane (5×100 ml). The remaining oil was dissolved in dichloromethane, washed with 5% $NaHCO_3$ solution, dried ($Na_2SO_4$), filtered and evaporated to dryness. The residual oil was chromatographed on silica gel (Waters Prep 500), eluting with a linear gradient of 3:1 toluene-ethyl acetate (4 liters) and ethyl acetate (4 liters). Fractions containing the desired product were located by TLC analysis, combined and evaporated under reduced pressure; the residual solid was washed with hexane, filtered and air-dried to give 3.4 g (69%) of compound 37.

EXAMPLE 9

2',4'-Di-O-acetyl-23-O-(D-mandeloyl)-OMT (Compound 41)

D-Mandelic acid (3.04 g, 20 mmol) and N-hydroxysuccinimide (2.3 g, 20 mmol) were dissolved in dichloromethane (110 ml) and treated with N,N'-dicyclohexylcarbodiimide (4.12 g, 20 mmol). After stirring for 30 minutes at room temperature, 2',4'-di-O-acetyl-OMT (5.0 g, 7.35 mmol) and pyridine (50 ml) were added. The mixture was stirred for 4.5 days at room temperature with exclusion of moisture. Methanol (10 ml) was added to decompose remaining active esters. After stirring for 1 hour, the mixture was concentrated under reduced pressure, diluted with toluene and evaporated to dryness. The residue was taken up with toluene and filtered. The filtrate was concentrated under reduced pressure. The concentrate was chromatographed on a column of silica gel (Waters Prep 500), eluting with a linear gradient of toluene (4 liters) and ethyl acetate (4 liters). Fractions containing the desired product were located by TLC analysis, combined and evaporated to dryness to yield 1.05 g of 2',4'-di-O-acetyl-23-O-(mandeloyl)-OMT (41).

EXAMPLE 10

2',4'-Di-O-acetyl-23-O-(N-t-BOC-phenylglycyl)-OMT (Compound 39)

D-(-)-t-BOC-Phenylglycine (6.14 g, 24.5 mmol) and N-hydroxysuccinimide (2.8 g, 24.5 mmol) in dichloromethane (300 ml) were treated with N,N'-dicyclohexylcarbodiimide (5.05 g, 24.5 mmol) for 45 minutes at room temperature. 2',4'-Di-O-acetyl-OMT (8.4 g, 12.4 mmol) in dichloromethane (10 ml) and then pyridine (50 ml) were added. After stirring at room temperature for 1.5 days, the reaction was quenched by addition of methanol (20 ml). After stirring for 1.5 hours, the mixture was concentrated under reduced pressure, diluted with toluene, evaporated to near dryness, diluted again with toluene, filtered and concentrated to a smaller volume. This concentrate was loaded on a column of silica gel (Waters Prep 500); the column was eluted with a linear gradient of 3:1 toluene-ethyl acetate (4 liters) and ethyl acetate (4 liters). Fractions containing the desired products were located by TLC analysis, combined and evaporated to dryness to yield 5.1 g of compound 39.

EXAMPLE 11

2',4'-Di-O-acetyl-23O-(3-pyridylacetyl)-OMT (Compound 43)

1,1'-Carbonyldiimidazole (3.57 g, 22 mmol) was dissolved in anhydrous tetrahydrofuran (THF, 50 ml) and toluene (30 ml) under a $N_2$ atmosphere and treated with 3-pyridylacetic acid (2.74 g, 20 mmol). After stirring at room temperature for 30 minutes, evolution of $CO_2$ had ceased. An aliquot (44 ml, 1.5 equiv) of this solution was withdrawn via syringe and added to a solution of 2',4'-di-O-acetyl-OMT (5.0 g, 7.34 mmol) in anhydrous THF (50 ml). This mixture was heated at 85° for 3.5 hours, treated with another aliquot (10 ml) of the acylimidazole solution, and heated for 3 more hours. After stirring overnight at room temperature, the solution was concentrated under reduced pressure, diluted with toluene, reconcentrated, diluted with 2:1 toluene-ethyl acetate, washed with water, dried ($Na_2SO_4$), filtered and evaporated to dryness. The residue was purified by flash chromatography on silica gel (E. Merck 60); the column was packed in toluene and eluted first with a linear gradient of 1:1 toluene-ethyl acetate (1 liter) and ethyl acetate (1 liter) and then with ethyl acetate. Fractions containing the desired product were located by TLC analysis, combined and evaporated to dryness to yield 1.8 g (33%) of compound 43.

EXAMPLE 12

23-O-(p-Acetamidobenzenesulfonyl)-2',4'-di-O-acetyl-OMT (Compound 47)

2',4'-Di-O-acetyl-OMT (5.0 g, 7.35 mmol) was dissolved in dichloromethane (200 ml) and pyridine (25 ml) and then treated with p-acetamidobenzenesulfonyl chloride (1.9 g, 7.35 mmol). After stirring overnight at room temperature, additional p-acetamidobenzenesulfonyl chloride (1.0 g) was added. The reaction mixture was again stirred overnight at room temperature and then was poured into saturated $NaHCO_3$ solution; the organic layer was separated, dried ($Na_2SO_4$) and filtered; the filtrate was evaporated under reduced pressure. The residual gum was dissolved in a small volume of toluene-dichloromethane and purified by flash chromatography on silica gel (E. Merck 60). The column was eluted stepwise with mixtures of toluene-ethyl acetate (200 ml of 4:1, 300 ml of 3:1, 400 ml of 2:1, 300 ml of 1:1, 450 ml of 1:2) and finally with ethyl acetate. Fractions containing the desired product were located by TLC analysis, combined and evaporated to dryness to yield 4.1 g of compound 47.

EXAMPLE 13

23-O-Phenylacetyl-OMT (Compound 29)

2',4'-Di-O-acetyl-23-O-phenylacetyl-OMT (1.0 g), prepared as described in Example 5, was dissolved in 80% aqueous methanol (60 ml) and refluxed under an argon atmosphere for 1.5 hours. The solution was cooled, evaporated to remove the methanol and then was partitioned between dichloromethane and saturated $NaHCO_3$ solution. The organic layer was separated, dried ($Na_2SO_4$) and filtered. The filtrate was evaporated to dryness to yield quantitatively 23-O-phenylacetyl-OMT (29).

EXAMPLE 14

23-O-Acetyl-OMT (Compound 13)

2',4',23-Tri-O-acetyl-OMT (2.3 g), prepared as described in Example 2, was dissolved in 80% aqueous methanol (70 ml) and refluxed for 45 minutes. The solution was cooled and evaporated under reduced pressure. The residue was dissolved in dichloromethane, dried ($Na_2SO_4$) and filtered. The filtrate was evaporated to dryness. The residue was purified by flash chromatography on silica gel, eluting stepwise with ethyl acetate (300 ml), 3% ethanol in ethyl acetate (300 ml) and 5% ethanol in ethyl acetate (800 ml). Fractions containing the desired product were located by TLC analysis, combined and evaporated to dryness to yield 0.8 g of 23-O-acetyl-OMT (13).

EXAMPLE 15

23-O-Phenoxyacetyl-OMT (Compound 36)

2',4'-Di-O-acetyl-23-O-phenoxyacetyl-OMT (2.37 g), prepared according to the procedure of Example 7, was dissolved in 80% aqueous methanol (50 ml) and refluxed for 1 hour under an argon atmosphere. The solution was then cooled, concentrated to remove the methanol under reduced pressure, diluted with toluene, and evaporated to dryness. The residue was purified by flash chromatography on silica gel, eluting with a linear gradient of dichloromethane (1 liter) and 15% methanol in dichloromethane (1 liter). Fractions containing the desired product were located by TLC analysis, combined, and evaporated to dryness to yield 1.3 g of 23-O-phenoxyacetyl-OMT (36). Later fractions from the chromatographic separation yielded 0.5 g of OMT, obtained as a result of hydrolysis of the 23-O-phenoxyacetyl ester.

EXAMPLE 16

23-O-[(3,4-Dichlorophenylthio)acetyl]-OMT (Compound 38)

2',4'-Di-O-acetyl-23-O-[(3,4-dichlorophenylthio)acetyl]-OMT (2.0 g), prepared as described in Example 8, was dissolved in 80% aqueous methanol (80 ml) and heated at 80° under an argon atmosphere for 2 hours. The solution was cooled and evaporated under reduced pressure. The residue was dissolved in dichloromethane, dried (Na$_2$SO$_4$) and filtered. The filtrate was evaporated to dryness. The residue was dissolved in dichloromethane and purified by flash chromatography on silica gel, eluting stepwise with increasing amounts of methanol in dichloromethane (150 ml of 2%, 150 ml of 5%, and 450 ml of 7.5%). Fractions containing the desired product were located by TLC analysis, combined, and evaporated to dryness to yield 0.8 g of 23-O-[(3,4-dichlorophenylthio)acetyl]-OMT (38).

EXAMPLE 17

23-O-Benzoyl-OMT (Compound 26)

23-O-Benzoyl-2',4'-di-O-acetyl-OMT (700 mg), prepared as described in Example 6, was dissolved in 80% aqueous methanol (60 ml) and refluxed for 2 hours. The solution was cooled and evaporated to dryness under reduced pressure to yield 561 mg of 23-O-benzoyl-OMT (26).

EXAMPLE 18

23-O-Mandeloyl-OMT (Compound 42)

2',4'-Di-O-acetyl-23-O-mandeloyl-OMT (900 mg), prepared as described in Example 9, was dissolved in 80% aqueous methanol (30 ml) and heated at 85° for 1 hour. The solution was cooled and evaporated to dryness under reduced pressure. The residue was dissolved in dichloromethane, dried (Na$_2$SO$_4$) and filtered. The filtrate was evaporated to dryness to yield 750 mg of 23-O-mandeloyl-OMT (42).

EXAMPLE 19

23-O-(3-Pyridylacetyl)-OMT (Compound 44)

2',4'-Di-O-acetyl-23-O-(3-pyridylacetyl)-OMT (1.5 g), prepared as described in Example 11, was dissolved in 80% aqueous methanol (50 ml) and refluxed for 75 minutes. The solution was cooled and evaporated to dryness under reduced pressure. The residue was suspended in hexane and filtered. The insoluble material was washed with hexane and air-dried to yield 1.2 g of 23-O-(3-pyridylacetyl)-OMT (44).

EXAMPLE 20

23-O-(p-Acetamidobenzenesulfonyl)-OMT (Compound 56)

23-O-(p-Acetamidobenzenesulfonyl)-2',4'-di-O-acetyl-OMT (2.0 g), prepared as described in Example 12, was dissolved in 80% aqueous methanol (50 ml) and refluxed for 75 minutes. The solution was cooled and evaporated under reduced pressure. The residue was dissolved in dichloromethane, washed with saturated NaHCO$_3$ solution, dried (Na$_2$SO$_4$) and filtered. The filtrate was evaporated to dryness to give 1.7 g of 23-O-(p-acetamidobenzenesulfonyl)-OMT (56).

EXAMPLE 21

23-O-(D-t-BOC-Phenylglycyl)-OMT (Compound 40)

2',4'-Di-O-acetyl-23-O-(D-t-BOC-phenylglycyl)-OMT (3.9 g), prepared as described in Example 10, was dissolved in 80% aqueous methanol (70 ml) and refluxed for 75 minutes. The solution was cooled, concentrated to remove the methanol, poured into saturated NaHCO$_3$ solution and extracted with dichloromethane. The organic layer was separated, dried (Na$_2$SO$_4$), filtered and evaporated under reduced pressure to yield 3.0 g (84%) of 23-O-(D-t-BOC-phenylglycyl)-OMT (40).

EXAMPLE 22

23-O-(D-Phenylglycyl)-OMT bis-Trifluoroacetate Salt

23-O-(D-t-BOC-Phenylglycyl)-OMT (830 mg), prepared as described in Example 21, was cooled in an ice bath, dissolved in trifluoroacetic acid (5 ml) and stirred for 20 minutes. The solution was diluted with ether. The precipitate which formed was filtered, washed with ether and hexane and air-dried to yield 865 mg (90%) of the bis-trifluoroacetate salt of 23-O-(D-phenylglycyl)-OMT.

EXAMPLE 23

Alternate Preparation of 23-O-Acetyl-OMT (13)

OMT (5.0 g, 8.5 mmol) was dissolved in dichloromethane (100 ml) and 2,4,6-collidine (5 ml), cooled in an acetone-dry ice bath and treated with acetyl chloride (0.75 ml, 10.6 mmol). The cold bath was removed and the mixture was stirred while allowing it to warm to room temperature over a 45-minute period. The mixture was washed with saturated NaHCO$_3$ solution, dried (Na$_2$SO$_9$) and filtered. The filtrate was evaporated under reduced pressure. The residue was chromatographed on silica gel (Waters Prep 500), eluting with a linear gradient of dichloromethane (4 liters) and 15% methanol in dichloromethane (4 liters). Fractions containing the desired product were located by TLC analysis, combined and evaporated to dryness to yield 1.83 g of 23-O-acetyl-OMT (13).

EXAMPLE 24

Alternate Preparation of 23-O-Phenylacetyl-OMT (29)

OMT (3.0 g, 5.0 mmol) was dissolved in dichloromethane (50 ml) and 2,4,6-collidine (2.5 ml), cooled in an acetone-dry ice bath and treated with phenylacetyl chloride (0.83 ml, 6.3 mmol). The cold bath was removed, and the mixture was stirred while allowing it to warm to room temperature over a 30-minute period. The mixture was washed with saturated NaHCO$_3$ solution, dried (Na$_2$SO$_4$) and filtered. The filtrate was evaporated to dryness under reduced pressure. The residue was dissolved in a small volume of dichloromethane and purified by flash chromatography on silica gel (E. Merck 60), eluting with a linear gradient of dichloromethane (1 liter) and 15% methanol in dichloromethane (1 liter). Fractions containing the desired product were located by TLC analysis, combined and evaporated to dryness to yield 2.0 g (56%) of 23-O-phenylacetyl-OMT (29).

EXAMPLE 25

23-O-(Diphenylphosphoryl)-OMT (Compound 48)

OMT (4.0 g, 6.7 mmol) was dissolved in dichloromethane (10 ml) and pyridine (1 ml), cooled in an acetone-dry ice bath and treated with diphenyl chlorophosphate (3.6 g, 13.4 mmol). The cold bath was removed, the reaction was stirred and allowed to warm to room temperature over a 30-minute period. Since TLC analysis showed starting material was still present, the mixture was again cooled to −78° C., treated with diphenyl chlorophosphate (1.0 ml) and allowed to warm as before. The mixture was then washed with saturated $NaHCO_3$ solution, dried ($Na_2SO_4$) and filtered. The filtrate was evaporated under reduced pressure, diluted with dichloromethane-cyclohexane and re-evaporated. The crude product was purified by flash chromatography on silica gel (E. Merck 60), eluting with a linear gradient of dichloromethane (1 liter) and 15% methanol in dichloromethane (1 liter). Fractions containing the desired product were located by TLC analysis, combined and evaporated to dryness to yield 3.2 g (57%) of 23-O-diphenylphosphoryl-OMT (48).

EXAMPLE 26

2',4'-Di-O-benzoyl-OMT (Compound 5)

OMT (1.2 g, 2 mmol) was dissolved in acetone (100 ml) and treated with benzoic anhydride (1.8 g, 8 mmol) while stirring at room temperature. After 1.5 hours, solvent was evaporated under reduced pressure. The residue was dissolved in dichloromethane, washed with saturated $NaHCO_3$ solution, dried ($Na_2SO_4$) and filtered. The filtrate was evaporated to dryness. This residue was purified by flash chromatography on silica gel, eluting initially with 4:1 toluene-ethyl acetate (300 ml) and then with ethyl acetate. Fractions containing the desired product were located by TLC analysis, combined and evaporated to dryness to yield 1.04 g of 2',4'-di-O-benzoyl-OMT (5).

EXAMPLES 27–28

2',4',23-Tri-O-propionyl-OMT (Compound 8) and 23-O-Propionyl-OMT (Compound 14)

OMT (3.0 g, 5.0 mmol) was dissolved in dry pyridine (60 ml) and treated with propionic anhydride (2.3 ml, 17.1 mmol). After stirring overnight at room temperature with exclusion of moisture, solvent was evaporated under reduced pressure. The residual oil was dissolved in dichloromethane and washed with saturated $NaHCO_3$ solution; the organic layer was separated, dried ($Na_2SO_4$) and filtered. The filtrate was evaporated to dryness to give 3.7 g of 2',4',23-tri-O-propionyl-OMT (8).

A portion (1.25 g) of this invention was further purified by flash chromatography on silica gel, eluting with 3:1 toluene-ethyl acetate. Fractions containing the desired product were located by TLC analysis, combined, and evaporated to dryness to yield 565 mg of purified 2',4',23-tri-O-propionyl-OMT (8).

The remaining amount (2.4 g) of crude 2',4',23-tri-O-propionyl-OMT was dissolved in 80% aqueous methanol (100 ml) and refluxed for 70 minutes. The solution was cooled and evaporated under reduced pressure to a gummy residue which was dissolved in a small volume of dioxane and then lyophilized. The residue was purified by flash chromatography on silica gel, eluting with 4:1 ethyl acetate-absolute ethanol. Fractions containing the desired product were located by TLC analysis, combined, and evaporated to dryness to yield 0.74 g of 23-O-propionyl-OMT (14).

EXAMPLE 29

2'-O-Acetyl-OMT (Compound 1)

DMT (12.5 g) was dissolved in acetone (250 ml) and treated with acetic anhydride (5.0 ml) while stirring at room temperature with exclusion of moisture. After being stirred overnight, the solution was concentrated under reduced pressure and then was diluted with dichloromethane. This solution was extracted with saturated $NaHCO_3$ solution, dried ($Na_2SO_4$) and filtered. The filtrate was evaporated to dryness to give a residue containing 2'-O-acetyl-DMT. This residue was dissolved in 1 N sulfuric acid (225 ml), and the solution was stirred for 2 hours at room temperature. The solution was slowly and carefully poured into saturated $NaHCO_3$ solution (800 ml), and the product was extracted with dichloromethane (200, 300 ml). The organic layers were combined, extracted with saturated $NaHCO_3$ solution, dried ($Na_2SO_4$) and filtered. The filtrate was evaporated to dryness. The residue was suspended in hexane, filtered and dried to yield 10.4 g (96%) of 2'-O-acetyl-OMT (1).

EXAMPLE 30

2'-O-Propionyl-OMT (Compound 2)

DMT (6.0 g) was treated according to the method of Example 29, but using propionic anhydride (1.2 ml) and chromatographing the product on silica gel (Waters Prep 500) in ethyl acetate to give 2'-O-propionyl-DMT (3.7 g, 57% yield). 2'-O-Propionyl-DMT (1.0 g) thus prepared was dissolved in 95% aqueous ethanol (15 ml) and water (15 ml). The pH of this solution was adjusted to 2.0 by the addition of 0.1 N HCl; the solution was stirred at room temperature for 24 hours and worked up as described in Example 29. The residue obtained was chromatographed on silica gel (Waters Prep 500) in ethyl acetate, and the appropriate fractions were combined to give 284 mg of 2'-O-propionyl-OMT (2).

EXAMPLE 31

2'-O-Acetyl-4'-O-isovaleryl-OMT (Compound 49);
2'-O-Acetyl-4',23-di-O-isovaleryl-OMT (Compound 50) and
2',23-Di-O-Acetyl-4'-O-isovaleryl-OMT (Compound 51)

DMT (10 g, 13.5 mmol) was dissolved in acetone (260 ml) and treated with acetic acid anhydride (1.6 ml, 15.7 mmol) dropwise with stirring at room temperature. After stirring overnight (18 hours), the solvent was evaporated under reduced pressure. The residue thus obtained was dissolved in ethyl acetate (200 ml), and this solution was extracted with saturated $NaHCO_3$ solution (2×200 ml). The organic solution was dried ($Na_2SO_4$), filtered and evaporated. The residue was dissolved in a small volume of ethyl acetate, loaded on a silica gel column (Waters Prep 500) and eluted with ethyl acetate (4 liters). Fractions containing the desired product were identified by TLC, combined and evaporated to dryness, yielding 6.5 g (61%) of 2'-O-acetyl-DMT.

2'-O-Acetyl-DMT prepared by this method was treated using the method of Example 29 to give 2'-O-acetyl-OMT.

2'-O-Acetyl-OMT (1.0 g, 1.57 mmol) was dissolved in acetone (25 ml). Solid sodium bicarbonate (400 mg) was added, and the mixture was treated with isovaleryl chloride (0.25 ml, 2.04 mmol) while stirring at room temperature. After 1.5 hours, additional isovaleryl chloride (0.25 ml) was added to consume unreacted starting material. After 3.5 hours, starting material was absent (TLC analysis), and the mixture was poured into saturated NaHCO$_3$ solution (150 ml). The resulting solution was extracted twice with dichloromethane (100 ml). The extracts were combined, dried (Na$_2$SO$_4$) and filtered; the filtrate was evaporated to dryness. The residue was dissolved in a small volume of toluene and purified by flash chromatography on silica gel, eluting with a linear gradient of 3:1 toluene-ethyl acetate (1 liter) and ethyl acetate (1 liter). Fractions containing the desired products were located by TLC, combined and evaporated to dryness to yield 735 mg of 2'-acetyl-4'-O-isovaleryl-OMT(49), 78 mg of 2'-O-acetyl-4',23-di-O-isovaleryl-OMT(50), and 71 mg of 2',23-di-O-acetyl-4'-O-isovaleryl-OMT(51).

EXAMPLE 32

2'-O-Acetyl-23-O-propionyl-OMT (Compound 12)

2'-O-Acetyl-DMT (6 g, 7.7 mmol), prepared as described in Example 31, was dissolved in methylene chloride (180 ml) and pyridine (15 ml) and treated with propionic anhydride (1.2 ml, 9.2 mmol) dropwise with stirring at room temperature. After being stirred overnight (17 hours), the solution was diluted with toluene (300 ml) and evaporated to dryness under reduced pressure. The residue was dissolved in toluene, and this solution was extracted with saturated NaHCO$_3$ solution. The toluene layer was dried (Na$_2$SO$_4$), filtered and evaporated. The residue, dissolved in a small volume of toluene, was loaded onto a flash-chromatography column of silica gel (300 ml) packed in 1:1 toluene-ethyl acetate. The column was eluted with 1:1 toluene-ethyl acetate (1 liter). Fractions containing the desired product was identified by TLC, combined and evaporated under reduced pressure to yield 4.5 g (70%) of 2'-O-acetyl-23-O-propionyl-DMT.

2'-O-Acetyl-23-O-propionyl-DMT (489 mg) was dissolved in 95% ethanol (15 ml) and water (15 ml). The solution was adjusted to pH 2.0 with 1 N hydrochloric acid and stirred for 2 days at room temperature. The solution was concentrated to remove ethanol under reduced pressure, adjusted to pH 8.5 with 1 N sodium hydroxide and extracted with dichloromethane. The organic layer was separated, dried (Na$_2$SO$_4$) and filtered. The filtrate was evaporated under reduced pressure to give 270 mg of 2'-O-acetyl-23-O-propionyl-OMT(12).

EXAMPLE 33

Alternate Preparation of 23-O-Propionyl-OMT (Compound 14)

2'-O-Acetyl-23-O-propionyl-DMT (1.6 g, 1.9 mmol), prepared as described in Example 32, was dissolved in 95% MeOH (80 ml) and stirred at room temperature for 42 hours. The solution was evaporated to dryness under reduced pressure. The residue was dissolved in a small volume of toluene, loaded onto a flash-chromatography column of silica gel (E. Merck 60, 200 ml) and eluted with 1:1 toluene-ethyl acetate (2 liters). Fractions containing the desired product were identified by TLC, combined and evaporated under reduced pressure to yield 1.2 g (79%) of 23-O-propionyl-DMT.

23-O-Propionyl-DMT (678 mg) thus prepared was dissolved in 95% ethanol (10 ml) and water (10 ml). The solution was adjusted to pH 2.0 with 1 N hydrochloric acid and stirred overnight at room temperature. The solution was concentrated to remove ethanol under reduced pressure, diluted with water (20 ml), and washed with dichloromethane. The solution was then made basic (pH 8.5) with 1 N sodium hydroxide and extracted twice with dichloromethane (25 ml). The latter extracts were combined, dried (Na$_2$SO$_4$) and filtered. The filtrate was evaporated under reduced pressure to yield 331 mg of 23-O-propionyl-OMT(14).

EXAMPLE 34

2'-O-Acetyl-23-O-(p-chlorophenylacetyl)-OMT (Compound 31)

p-Chlorophenylacetic acid (4.3 g, 25 mmol) and 1-hydroxybenzotriazole (3.4 g, 25 mmol) were dissolved in THF (150 ml). The solution was cooled in an ice bath and treated with N,N'-dicyclohexylcarbodiimide (5.2 g, 25.3 mmol). The reaction mixture was stirred at 0° C. for 3 hours and then placed in a refrigerator overnight. The mixture was filtered, and the filtrate was evaporated under reduced pressure. The residue was dissolved in acetone (75 ml), filtered and treated with 2'-O-acetyl-DMT (10 g, 12.8 mmol) and imidazole (0.87 g, 12.8 mmol). Acetone was added to give a solution volume of 125 ml, and then triethylamine (1.87 ml, 12.8 mmol) was added. After the reaction was stirred for 20 hours at room temperature, the solvent was evaporated under reduced pressure. The residue was loaded on a flash-chromatography silica-gel column which was eluted with a gradient of 4:1 toluene-ethyl acetate to ethyl acetate alone. The desired fractions were combined on the basis of TLC results and evaporated to dryness to give 4.75 g of 2'-O-acetyl-23-O-(p-chlorophenylacetyl)-DMT.

2'-O-Acetyl-23-O-(p-chlorophenylacetyl)-DMT (4.35 g, 4.65 mmol) thus prepared was dissolved in 1 N sulfuric acid (175 ml) and stirred at room temperature for 1 hour. Saturated NaHCO$_3$ solution was carefully added until foaming ceased, and the product was extracted into dichloromethane. The organic layer was separated, dried (Na$_2$SO$_4$) and filtered; and the filtrate was evaporated under reduced pressure. The residue was purified by flash chromatography on silica gel, eluting initially with 4:1 toluene-ethyl acetate and subsequently increasing the proportion of ethyl acetate up to 100%. Fractions containing the desired product were located by TLC, combined and evaporated to dryness to yield 3.1 g of 2'-O-acetyl-23-O-(p-chlorophenylacetyl)-OMT (31).

EXAMPLE 35

23-O-(p-Chlorophenylacetyl)-OMT (Compound 32)

2'-O-Acetyl-23-O-(p-chlorophenylacetyl)-OMT (1.88 g, 2.37 mmol), prepared as described in Example 34, was dissolved in 80% aqueous methanol (113 ml); the solution was stirred at 80° for 40 minutes. The solution was cooled, concentrated to remove the methanol under reduced pressure and diluted with saturated NaHCO$_3$ solution. The resulting solution was extracted with dichloromethane. The organic layer was separated, dried (Na₂SO₄) and filtered. The filtrate was evaporated under reduced pressure to yield 1.70 g of 23-O-(p-chlorophenylacetyl)-OMT (32).

EXAMPLE 36

2',23-Di-O-Propionyl-OMT (Compound 10)

DMT (3 g, 4.05 mmol) was dissolved in methylene chloride (90 ml) and pyridine (7.8 ml) and treated with propionic anhydride (1.8 ml, 13.8 mmol) dropwise with stirring at room temperature. After the reaction was stirred overnight, toluene (15 ml) was added. The resulting solution was evaporated to dryness under reduced pressure. The residue, dissolved in toluene (20 ml), was loaded onto a flash-chromatography column of silica gel (E. Merck 60, 300 ml) which was eluted sequentially with 3:1 toluene-ethyl acetate (300 ml), 5:4 toluene-ethyl acetate (300 ml), and 1:1 toluene-ethyl acetate (1000 ml). Fractions were combined on the basis of TLC results and evaporated to dryness to give 2.5 g (72%) of 2',23-di-O-propionyl-DMT.

2',23-Di-O-Propionyl-DMT (1.4 g) thus prepared was dissolved in 1 N sulfuric acid (60 ml) and stirred for 2 hours at room temperature. The solution was carefully poured into saturated NaHCO₃ solution, and the product was extracted from this solution with dichloromethane (3×). The organic extracts were combined, dried (Na₂SO₄) and evaporated to dryness under reduced pressure. The product was purified by chromatography on silica gel (Waters Prep 500), eluting with a linear gradient of 4:1 toluene-ethyl acetate (4 liters) and ethyl acetate (4 liters). Fractions containing the desired product were located by TLC, combined and evaporated to dryness to yield 201 mg of 2',23-di-O-propionyl-OMT (10).

EXAMPLES 37–38

2'-O-(Phenylacetyl)-OMT (Compound 52);
2',23-Di-O-Phenylacetyl-OMT (Compound 53)

Phenylacetic acid (2.72 g, 27 mmol) was dissolved in 1:1 tetrahydrofuran:acetonitrile (50 ml) and treated with N,N'-dicyclohexylcarbodiimide (2.79 g, 13.5 mmol). The reaction mixture was stirred overnight at room temperature. A precipitate which formed was removed by filtration. The filtrate was treated with DMT (10 g, 13.5 mmol) and pyridine (10 ml). After being stirred at room temperature for 40 hours, the mixture was evaporated under reduced pressure. The residue was dissolved in dichloromethane, and the solution was washed with saturated NaHCO₃ solution. The organic layer was separated, dried (Na₂SO₄) and filtered; and the filtrate was evaporated to dryness. The residue obtained was purified by flash chromatography on silica gel, eluting stepwise with toluene:ethyl acetate (2:1, 1:1, 2:3) and finally with ethyl acetate. Fractions were analyzed by TLC. Appropriate fractions were combined and evaporated to dryness. The first product eluted was 2',23-di-O-phenylacetyl-DMT (271 mg).

Later fractions yielded a mixture of DMT and its 2'-O-phenylacetyl derivative (3.97 g). This mixture was separated further by flash chromatography on silica gel, eluting with toluene:ethyl acetate (500 ml of 2:1, 600 ml of 1:1, 600 ml of 1:2) and then ethyl acetate (1 liter). The partially purified fractions were combined according to TLC analysis and then further purified by another chromatography on silica gel (Waters Prep 500), eluting with a linear gradient of 3:1 toluene:ethyl acetate and ethyl acetate. The fractions of pure product were combined and evaporated to dryness to give 478 mg of 2'-O-phenylacetyl-DMT.

Other fractions from this column contained a mixture of 2'-O-phenylacetyl-DMT and DMT. This mixture (610 mg) was dissolved in 1 N sulfuric acid and stirred for 1.5 hours at room temperature. NaHCO₃ was carefully added until gas evolution ceased. The product was extracted with dichloromethane; and the organic layer was separated, dried (Na₂SO₄) and filtered. The filtrate was evaporated under reduced pressure. The residue obtained was purified by flash chromatography on silica gel, eluting stepwise with toluene:ethyl acetate (400 ml of 2:1, 600 ml of 1:1, 600 ml of 1:2, 400 ml of 1:3) and finally ethyl acetate (600 ml). Fractions containing the desired product were located by TLC, combined and evaporated to dryness to yield 330 mg of 2'-O-phenylacetyl-OMT (52).

2',23-Di-O-Phenylacetyl-DMT (1.0 g) prepared in this manner was treated with 1 N sulfuric acid (40 ml) in a similar manner to give 271 mg of 2',23-di-O-phenylacetyl-OMT (53).

EXAMPLE 39

Injectable Formulations (A) A formula 1 base is added to propylene glycol. Water and benzyl alcohol are added so that the solution contains 50% (by volume) propylene glycol, 4% (by volume) benzyl alcohol, and 200 mg/ml of a formula 1 base.

(B) A solution is prepared as described in Section A except that the solution contains 50 mg/ml of a formula 1 base.

(C) A solution is prepared as described in Section A except that the solution contains 350 mg/ml of a formula 1 base.

(D) A solution is prepared as described in Section A except that the solution contains 500 mg/ml of a formula 1 tartrate.

(E) A suspension is prepared by adding a finely ground formula 1 compound to carboxymethyl cellulose with thorough mixing so that the suspension contains 200 mg of the formula 1 base per ml of suspension.

I claim:

1. A compound of the formula

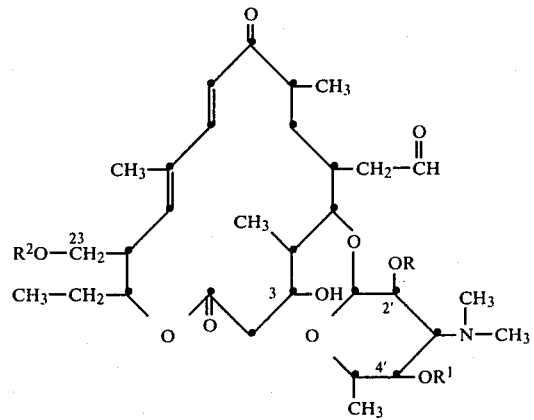

wherein R and R¹ are selected from hydrogen, C₁–C₅-alkanoyl, C₁–C₅-alkanoyl having from one to three halo substituents, benzoyl, phenylacetyl or phenylpropionyl or benzoyl, phenylacetyl, or phenylpropionyl each having on the phenyl ring from one to five halo or methyl or from one to two methoxyl, nitro or hydroxyl groups; $R^2$ is hydrogen or an acyl group selected from:

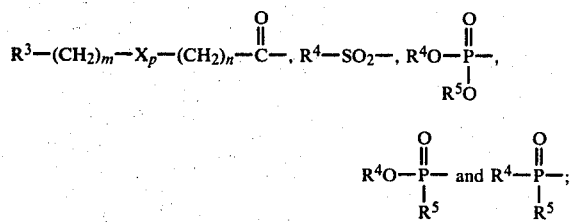

p is 0 or 1; and m and n are integers from 0 to 4; $R^3$ is hydrogen, halo, $C_1$–$C_4$-alkyl, $C_3$–$C_8$-cycloalkyl, phenyl, $C_5$–$C_8$-cycloalkenyl, naphthyl, indenyl, tetralinyl, decalinyl, adamantyl, 1-ethyl-1,4-dihydro-4-oxo[1,3]dioxolo[4,5-g]cinnolin-3-yl, a monocyclic heterocyclic ring system comprising 3 to 8 atoms or a bicyclic heterocyclic ring system comprising 6 to 11 atoms, provided that at least 1 atom of the ring system is carbon and at least 1 atom of the ring system is a heteroatom selected from O, N, and S; and wherein $R^3$ and the connecting alkyl groups $-(CH_2)_m-$ and $-(CH_2)_n-$ can have one or two halo, methyl, ethyl, methoxy, amino, tert-butoxycarbonylamino, methylamino, dimethylamino, nitro, acetoxy, acetamido, azido, carbomethoxy, carboxamido, cyano, or hydroxyl groups, provided that, when the substituent is other than halo or alkyl, there can be no more than one substituent on any connecting $-CH_2-$ group; X is O, S, $-NH-$, $-N(CH_3)-$, $-C\equiv C-$, $-CH=CH-$, $-C(CH_3)=CH-$, $-CH=C(CH_3)-$ or $-C(CH_3)=C(CH_3)-$; $R^4$ and $R^5$ are $C_1$–$C_5$-alkyl, phenyl or benzyl or phenyl or benzyl each having on the phenyl ring from one to five halo or methyl or from one to two methoxy, nitro or hydroxyl groups; provided that at least one of R, $R^1$ and $R^2$ must be other than hydrogen and that, when $R^1$ is other than hydrogen, R must also be other than hydrogen; and the acid addition salts thereof.

2. A compound of claim 1 wherein $R^2$ is an acyl group and the acid addition salts thereof.

3. A compound of claim 2 wherein the acyl group is

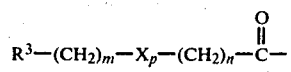

and the acid addition salts thereof.

4. A compound of claim 3 wherein $R^3$ is hydrogen, halo or $C_1$–$C_4$-alkyl and the acid addition salts thereof.

5. A compound of claim 4 wherein p is 0 and the acid addition salts thereof.

6. A compound of claim 3, 4, or 5 wherein R is $C_1$–$C_5$-alkanoyl and the acid addition salts thereof.

7. A compound of claim 6, wherein $R^1$ is $C_1$–$C_5$-alkanoyl and the acid addition salts thereof.

8. A compound of claim 6 wherein $R^1$ is hydrogen and the acid addition salts thereof.

9. A compound of claim 3, 4, or 5 wherein R and $R^1$ are hydrogen and the acid addition salts thereof.

10. A compound of claim 5 wherein $R^2$ is acetyl and the acid addition salts thereof.

11. The compound of claim 10 wherein R and $R^1$ are acetyl and its acid addition salts.

12. The compound of claim 10 wherein R is acetyl and $R^1$ is hydrogen and its acid additions salts.

13. The compound of claim 10 wherein R is propionyl and $R^1$ is hydrogen and its acid addition salts.

14. The compound of claim 10 wherein R and $R^1$ are hydrogen and its acid addition salts.

15. A compound of claim 5 wherein $R^2$ is propionyl and the acid addition salts thereof.

16. The compound of claim 15 wherein R and $R^1$ are propionyl and its acid addition salts.

17. The compound of claim 15 wherein R is propionyl and $R^1$ is hydrogen and its acid addition salts.

18. The compound of claim 15 wherein R is acetyl and $R^1$ is hydrogen and its acid addition salts.

19. The compound of claim 15 wherein R and $R^1$ are hydrogen and its acid addition salts.

20. A compound of claim 5 wherein $R^2$ is n-butyryl or i-butyryl and the acid addition salts thereof.

21. The compound of claim 20 wherein R and $R^1$ are acetyl and its acid addition salts.

22. The compound of claim 20 wherein R and $R^1$ are hydrogen and its acid addition salts.

23. The compound of claim 20 wherein R is acetyl and $R^1$ is hydrogen and the acid addition salts thereof.

24. A compound of claim 5 wherein $R^2$ is n-valeryl or i-valeryl and the acid addition salts thereof.

25. The compound of claim 24 wherein R and $R^1$ are acetyl and its acid addition salts.

26. The compound of claim 24 wherein R and $R^1$ are hydrogen and its acid addition salts.

27. The compound of claim 24 wherein R is acetyl and $R^1$ is hydrogen and its acid addition salts.

28. A compound of claim 5 wherein $R^2$ is pivaloyl and the acid addition salts thereof.

29. The compound of claim 28 wherein R and $R^1$ are acetyl and its acid addition salts.

30. The compound of claim 28 wherein R and $R^1$ are hydrogen and its acid addition salts.

31. The compound of claim 28 wherein R is acetyl and $R^1$ is hydrogen and its acid addition salts.

32. A compound of claim 5 wherein $R^2$ is n-octanoyl and the acid addition salts thereof.

33. The compound of claim 32 wherein R and $R^1$ are acetyl and its acid addition salts.

34. The compound of claim 32 wherein R and $R^1$ are hydrogen and its acid addition salts.

35. The compound of claim 32 wherein R is acetyl and $R^1$ is hydrogen and its acid addition salts.

36. A compound of claim 5 wherein $R^2$ is dichloroacetyl and the acid addition salts thereof.

37. A compound of claim 5 wherein $R^2$ is trichloroacetyl and its acid addition salts.

38. A compound of claim 5 wherein $R^2$ is 4-carbomethoxy-n-butyryl and its acid addition salts.

39. A compound of claim 3 wherein $R^2$ is methoxycarbonyl and its acid addition salts.

40. A compound of claim 3 wherein $R^3$ is phenyl or phenyl having from one to five halo or methyl or from one to two methoxy, nitro or hydroxyl groups and the acid addition salts thereof.

41. A compound of claim 40 wherein R is $C_1$–$C_5$-alkanoyl and the acid addition salts thereof.

42. A compound of claim 41 wherein $R^1$ is $C_1$–$C_5$-alkanoyl and the acid addition salts thereof.

43. A compound of claim 41 wherein $R^1$ is hydrogen and the acid addition salts thereof.

44. A compound of claim 40 wherein R and $R^1$ are hydrogen and the acid addition salts thereof.

45. A compound of claim 40 wherein $R^2$ is benzoyl and the acid addition salts thereof.

46. The compound of claim 45 wherein R and $R^1$ are acetyl and its acid addition salts.

47. The compound of claim 45 wherein R and $R^1$ are hydrogen and its acid addition salts.

48. A compound of claim 40 wherein $R^2$ is phenylacetyl and the acid addition salts thereof.

49. The compound of claim 48 wherein R and $R^1$ are acetyl and its acid addition salts.

50. The compound of claim 48 wherein R is acetyl and $R^1$ is hydrogen and its acid addition salts.

51. The compound of claim 48 wherein R and $R^1$ are hydrogen and its acid addition salts.

52. A compound of claim 40 wherein $R^2$ is phenylpropionyl and the acid addition salts thereof.

53. The compound of claim 52 wherein R and $R^1$ are acetyl and its acid addition salts.

54. The compound of claim 52 wherein R is acetyl and $R^1$ is hydrogen and its acid addition salts.

55. The compound of claim 52 wherein R and $R^1$ are hydrogen and its acid addition salts.

56. A compound of claim 40 wherein $R^2$ is (p-chlorophenyl)acetyl and the acid addition salts thereof.

57. The compound of claim 56 wherein R is acetyl and $R^1$ is hydrogen and its acid addition salts.

58. The compound of claim 56 wherein R and $R^1$ are hydrogen and its acid addition salts.

59. A compound of claim 40 wherein $R^2$ is cinnamoyl and the acid addition salts thereof.

60. The compound of claim 59 wherein R is acetyl and $R^1$ is hydrogen and its acid addition salts.

61. The compound of claim 59 wherein R and $R^1$ are hydrodgen and its acid addition salts.

62. A compound of claim 40 wherein $R^2$ is phenoxyacetyl and the acid addition salts thereof.

63. The compound of claim 62 wherein R and $R^1$ are acetyl and its acid addition salts.

64. The compound of claim 62 wherein R is acetyl and $R^1$ is hydrogen and its acid addition salts.

65. The compound of claim 62 wherein R and $R^1$ are hydrogen and its acid addition salts.

66. A compound of claim 40 wherein $R^2$ is [(3,4-dichlorophenyl)thio]acetyl and the acid addition salts thereof.

67. The compound of claim 66 wherein R and $R^1$ are acetyl and the acid addition salts thereof.

68. The compound of claim 66 wherein R and $R^1$ are hydrogen and its acid addition salts.

69. A compound of claim 40 wherein $R^2$ is N-(t-butoxycarbonyl)phenylglycyl and the acid addition salts thereof.

70. The compound of claim 69 wherein R and $R^1$ are acetyl and its acid addition salts.

71. The compound of claim 69 wherein R and $R^1$ are hydrogen and its acid addition salts.

72. A compound of claim 40 wherein $R^2$ is α-hydroxyphenylacetyl and the acid addition salts thereof.

73. The compound of claim 72 wherein R and $R^1$ are hydrogen and its acid addition salts.

74. A compound of claim 40 wherein $R^2$ is phenylglycyl and the acid addition salts thereof.

75. The compound of claim 74 wherein R and $R^1$ are hydrogen and its acid addition salts.

76. A compound of claim 40 wherein $R^2$ is 2,5-dimethoxyphenylacetyl and its acid addition salts.

77. A compound of claim 40 wherein $R^2$ is p-nitrophenylacetyl and the acid addition salts thereof.

78. A compound of claim 40 wherein $R^2$ is p-hydroxyphenylacetyl and the acid addition salts thereof.

79. A compound of claim 40 wherein $R^2$ is benzylaminocarbonyl and the acid addition salts thereof.

80. A compound of claim 3 wherein $R^3$ is a heterocyclic ring system or a heterocyclic ring system having one or two halo, methyl, ethyl, methoxy, amino, tert-butoxycarbonylamino, methylamino, dimethylamino, nitro, acetoxy, acetamido, azido, carbomethoxy, carboxamido, cyano, or hydroxyl groups and the acid addition salts thereof.

81. A compound of claim 80 wherein $R^2$ is 3-pyridylacetyl and the acid addition salts thereof.

82. A compound of claim 80 or 81 wherein R and $R^1$ are acetyl and its acid addition salts.

83. A compound of claim 80 or 81 wherein R and $R^1$ are hydrogen and its acid addition salts.

84. A compound of claim 3 wherein $R^3$ is $C_3$-$C_8$-cycloalkyl and the acid addition salts thereof.

85. A compound of claim 84 wherein $R^3$ is cyclohexyl and the acid addition salts thereof.

86. A compound of claim 3 wherein $R^2$ is naphthoyl and the acid addition salts thereof.

87. A compound of claim 3 wherein $R^2$ is 1-adamantylcarbonyl and the acid addition salts thereof.

88. A compound of claim 2 wherein the acyl group is $R^4$—$SO_2$— and the acid addition salts thereof.

89. A compound of claim 88 wherein $R^4$ is $C_1$-$C_5$-alkyl and the acid addition salts thereof.

90. A compound of claim 89 wherein $R^2$ is methanesulfonyl and the acid addition salts thereof.

91. A compound of claim 89 or 90 wherein R and $R^1$ are acetyl and its acid addition salts.

92. A compound of claim 89 or 90 wherein R and $R^1$ are hydrogen and its acid addition salts.

93. A compound of claim 88 wherein $R^4$ is phenyl or phenyl having from one to five halo or methyl or from one to two methoxy, nitro or hydroxyl groups and the acid addition salts thereof.

94. A compound of claim 93 wherein $R^2$ is p-toluenesulfonyl and its acid addition salts.

95. A compound of claim 93 wherein $R^2$ is p-acetamidobenzenesulfonyl and its acid addition salts.

96. A compound of claim 93, 94 or 95 wherein R and $R^1$ are acetyl and its acid addition salts.

97. A compound of claim 93, 94 or 95 wherein R and $R^1$ are hydrogen and its acid addition salts.

98. A compound of claim 2 wherein $R^2$ is

and the acid addition salts thereof.

99. A compound of claim 98 wherein $R^4$ and $R^5$ are $C_1$-$C_5$-alkyl and the acid addition salts thereof.

100. A compound of claim 98 wherein $R^4$ and $R^5$ are phenyl or benzyl or phenyl or benzyl having on the phenyl ring from one to five halo or methyl or from one to two methoxy, nitro or hydroxyl groups and the acid addition salts thereof.

101. A compound of claim 100 wherein $R^4$ and $R^5$ are phenyl and the acid addition salts thereof.

102. A compound of claim 98, 99, or 100 wherein R and $R^1$ are acetyl and its acid addition salts.

103. A compound of claim 98, 99, or 100 wherein R and $R^1$ are hydrogen and its acid addition salts.

104. A compound of claim 1 wherein $R^2$ is hydrogen and the acid addition salts thereof.

105. A compound of claim 104 wherein R is $C_1$-$C_5$-alkanoyl and the acid addition salts thereof.

106. A compound of claim 105 wherein $R^1$ is $C_1$-$C_5$-alkanoyl and the acid addition salts thereof.

107. The compound of claim 105 wherein R is acetyl and $R^1$ is hydrogen and its acid addition salts.

108. The compound of claim 106 wherein R and $R^1$ are acetyl and its acid addition salts.

109. The compound of claim 105 wherein R is propionyl and $R^1$ is hydrogen and its acid addition salts.

110. The compound of claim 106 wherein R and $R^1$ are propionyl and its acid addition salts.

111. A compound of claim 104 wherein R is benzoyl or benzoyl having on the phenyl ring from one to five halo or methyl or from one to two methoxy, nitro or hydroxyl groups and the acid addition salts thereof.

112. The compound of claim 111 wherein R is benzoyl and $R^1$ is hydrogen and its acid addition salts.

113. The compound of claim 111 wherein R and $R^1$ are benzoyl and its acid addition salts.

114. A compound of claim 104 wherein R is phenylacetyl or phenylacetyl having on the phenyl ring from one to five halo or methyl or from one to two methoxy, nitro or hydroxyl groups and the acid addition salts thereof.

115. The compound of claim 114 wherein R is phenylacetyl and $R^1$ is hydrogen and its acid addition salts.

116. The compound of claim 114 wherein R and $R^1$ are phenylacetyl and its acid addition salts.

117. A method for controlling Pasteurella infections which comprises administering to an infected or susceptible warm-blooded animal an effective amount of a composition comprising a compound of claim 1, 2, 3, 4, 5, 40, 80, 84, 88, 98 or 104 or a pharmaceutically acceptable acid addition salt thereof and a suitable pharmaceutical vehicle.

118. A composition for the control of gram-positive infections comprising an amount of a compound of claim 1, 2, 3, 4, 5, 40, 80, 84, 88, 98, or 104 or a pharmaceutically acceptable acid addition salt thereof which is effective against such infections and a suitable pharmaceutical vehicle.

119. A composition for the control of Pasteurella infections comprising an amount of a compound of claim 1, 2, 3, 4, 5, 40, 80, 84, 88, 98, or 104 or a pharmaceutically acceptable acid addition salt thereof which is effective against Pasteurella infections and a suitable pharmaceutical vehicle.

* * * * *